(12) United States Patent
Roeder et al.

(10) Patent No.: US 11,446,168 B2
(45) Date of Patent: Sep. 20, 2022

(54) PROSTHESIS WITH SIDE BRANCH AND METHOD OF MAKING THE SAME

(71) Applicant: Cook Medical Technologies LLC, Bloomington, IN (US)

(72) Inventors: Blayne A Roeder, Bloomington, IN (US); Jarin A Kratzberg, West Lafayette, IN (US); Charles L Baxter, West Lafayette, IN (US); Chantelle King, Brisbane (AU); Stephan Haulon, Lille (FR)

(73) Assignee: Cook Medical Technologies LLC, Bloomington, IN (US)

( * ) Notice: Subject to any disclaimer, the term of this patent is extended or adjusted under 35 U.S.C. 154(b) by 158 days.

(21) Appl. No.: 15/959,541

(22) Filed: Apr. 23, 2018

(65) Prior Publication Data
US 2018/0303641 A1 Oct. 25, 2018

Related U.S. Application Data

(60) Provisional application No. 62/489,619, filed on Apr. 25, 2017.

(51) Int. Cl.
*A61F 2/07* (2013.01)
*A61F 2/856* (2013.01)
(Continued)

(52) U.S. Cl.
CPC ............... *A61F 2/885* (2013.01); *A61F 2/07* (2013.01); *A61F 2/856* (2013.01); *A61F 2/915* (2013.01);
(Continued)

(58) Field of Classification Search
CPC ..... A61F 2/856; A61F 2/954; A61F 2002/061; A61F 2230/0091
See application file for complete search history.

(56) References Cited

U.S. PATENT DOCUMENTS 6,645,242 B1  11/2003  Quinn
6,827,735 B2  12/2004  Greenberg
(Continued)

FOREIGN PATENT DOCUMENTS

WO  WO 2009/020653 A1  2/2009

OTHER PUBLICATIONS

European Search Report for corresponding European Application No. 18275056, dated Sep. 3, 2018, 6 pages.
(Continued)

*Primary Examiner* — Martin T Ton
(74) *Attorney, Agent, or Firm* — Crowell & Moring LLP

(57) ABSTRACT

Prostheses and methods of making the same are provided. The prosthesis has an internal branch configuration. A trough or branch opening is at least partially defined by a trough wall extending into a main lumen from a sidewall of the prosthesis. The internal branch extends from the trough within the main lumen towards one of the outflow end of the graft body in a helical, retrograde arrangement. Other arrangements are described. The prosthesis may include a scalloped fenestration having a width larger than the trough. The trough may be positioned along a tapered region of the prosthesis. The trough and internal branch may be made from the same graft material. The trough and internal branch, in addition to the main graft body, may be made from the same graft material.

16 Claims, 11 Drawing Sheets

(51) Int. Cl.
*A61F 2/88* (2006.01)
*A61F 2/915* (2013.01)
*A61F 2/954* (2013.01)
*A61F 2/958* (2013.01)
*A61F 2/89* (2013.01)
*A61F 2/06* (2013.01)

(52) U.S. Cl.
CPC .............. *A61F 2/89* (2013.01); *A61F 2/954* (2013.01); *A61F 2/958* (2013.01); *A61F 2002/061* (2013.01); *A61F 2002/91558* (2013.01); *A61F 2230/0091* (2013.01); *A61F 2240/001* (2013.01); *A61F 2250/006* (2013.01); *A61F 2250/0039* (2013.01)

(56) References Cited

U.S. PATENT DOCUMENTS

| | | |
|---|---|---|
| 7,105,020 B2 | 9/2006 | Greenberg et al. |
| 7,108,715 B2 | 9/2006 | Lawrence-Brown et al. |
| 7,407,509 B2 | 8/2008 | Greenberg et al. |
| 7,413,573 B2 | 9/2008 | Hartley et al. |
| 7,550,004 B2 | 6/2009 | Bahler et al. |
| 7,645,298 B2 | 1/2010 | Hartley et al. |
| 7,670,369 B2 | 3/2010 | Schaeffer |
| 7,833,259 B2 | 11/2010 | Boatman |
| 7,887,576 B2 | 2/2011 | Bahler et al. |
| 7,998,186 B2 | 8/2011 | Hartley |
| 8,043,363 B2 | 10/2011 | Schaeffer |
| 8,226,706 B2 | 7/2012 | Hartley et al. |
| 8,394,136 B2 | 3/2013 | Hartley et al. |
| 8,758,425 B2 | 6/2014 | Greenberg et al. |
| 8,771,336 B2 | 7/2014 | Roeder |
| 8,795,349 B2 | 8/2014 | Huser et al. |
| 8,808,351 B2 | 8/2014 | Osborne |
| 8,808,355 B2 | 8/2014 | Barrand |
| 8,870,939 B2 | 10/2014 | Roeder et al. |
| 8,894,701 B2 | 11/2014 | Vad |
| 8,906,086 B2 | 12/2014 | Roeder et al. |
| 8,915,956 B2 | 12/2014 | Schaeffer et al. |
| 8,992,593 B2 | 3/2015 | Chuter et al. |
| 9,005,268 B2 | 4/2015 | Hartley et al. |
| 9,005,271 B2 | 4/2015 | Ivancev et al. |
| 9,011,517 B2 | 4/2015 | Hartley et al. |
| 9,034,027 B2 | 5/2015 | Ivancev |
| 9,060,887 B2 | 6/2015 | Hartley et al. |
| 9,072,621 B2 | 7/2015 | Hartley et al. |
| 9,078,780 B2 | 7/2015 | Schaeffer et al. |
| 9,095,456 B2 | 8/2015 | Ivancev et al. |
| 9,095,458 B2 | 8/2015 | Hartley et al. |
| 9,095,461 B2 | 8/2015 | Schaeffer |
| 9,101,455 B2 | 8/2015 | Roeder et al. |
| 9,101,456 B2 | 8/2015 | Hartley et al. |
| 9,107,741 B2 | 8/2015 | Bui et al. |
| 9,149,355 B2 | 10/2015 | Hartley |
| 9,149,382 B2 | 10/2015 | Greenberg et al. |
| 9,155,611 B2 | 10/2015 | Sun |
| 9,277,984 B2 | 3/2016 | Huser et al. |
| 9,351,822 B2 | 5/2016 | Roeder |
| 9,439,793 B2 | 9/2016 | Roeder |
| 9,649,188 B2 | 5/2017 | Hartley |
| 10,231,822 B2 | 3/2019 | Hartley |
| 10,285,799 B2 | 5/2019 | Hartley et al. |
| 10,485,651 B2 | 11/2019 | Hartley |
| 10,631,972 B2 | 4/2020 | Greenberg et al. |
| 10,729,532 B2 | 8/2020 | Eaton et al. |
| 2006/0247761 A1* | 11/2006 | Greenberg ............... A61F 2/07 623/1.16 |
| 2009/0043377 A1 | 2/2009 | Greenberg et al. |
| 2011/0270376 A1 | 11/2011 | Hartley |
| 2012/0041535 A1 | 2/2012 | Huser et al. |
| 2012/0197382 A1* | 8/2012 | Roeder ............... A61F 2/07 623/1.13 |
| 2013/0079870 A1* | 3/2013 | Roeder ............... A61F 2/07 623/1.35 |
| 2015/0034217 A1 | 2/2015 | Vad |
| 2015/0073534 A1 | 3/2015 | Roeder et al. |
| 2015/0112420 A1 | 4/2015 | Hartley et al. |
| 2015/0148890 A1 | 5/2015 | Hartley et al. |
| 2015/0305852 A1 | 10/2015 | Hartley et al. |
| 2015/0327983 A1 | 11/2015 | Roeder et al. |
| 2015/0374487 A1 | 12/2015 | Greenberg et al. |
| 2016/0022411 A1 | 1/2016 | Greenberg et al. |
| 2016/0106564 A1* | 4/2016 | Roeder ............... A61F 2/966 623/1.12 |
| 2016/0184081 A1 | 6/2016 | Huser et al. |
| 2018/0071125 A1 | 3/2018 | Bradway et al. |
| 2018/0116783 A1 | 5/2018 | Kratzberg et al. |

OTHER PUBLICATIONS

European Search Report for corresponding European Application No. 20209914, dated Mar. 9, 2021, 4 pages.
Examination Report for EP Application No. 20209914.9, dated Oct. 26, 2021, 4 pages.

* cited by examiner

PROSTHESIS WITH SIDE BRANCH AND METHOD OF MAKING THE SAME

RELATED APPLICATIONS

This application claims the benefit of priority of U.S. Provisional Application Ser. No. 62/489,619 filed Apr. 25, 2017, which is incorporated by reference in its entirety.

BACKGROUND

The present disclosure relates generally to medical devices for implantation within a human or animal body for repair of damaged vessels, ducts, or other physiological pathways, and particularly, to prostheses with side branch lumens.

Endovascular methods have been proposed for treatment of diseases of the aorta such as aortic dissection and aortic aneurysm. Using prostheses, such as stent grafts, to treat aneurysms is common in the medical field. Stent grafts are deployed by accessing a vasculature with a small incision in the skin and guiding a delivery system to the target area. This endoluminal delivery is less invasive and generally preferred over more intrusive forms of surgery. Multiple stent grafts may be implanted using endoluminal delivery to provide a system of interconnected stent grafts. Interconnected stent grafts can be made of fenestrated stent grafts and smaller side branch grafts, including bifurcated components.

Such methods have been proposed particularly when the diseased portion of the aorta is adjacent the aorta bifurcation. But when the diseased portion of the aorta is located higher up in the aorta, for example, in the region of the descending aorta adjacent the aortic arch or in the ascending aorta, endovascular techniques for treating these diseases are somewhat more difficult because of the arched or curved nature of the aortic arch, the presence of major arteries in the region, and the proximity to the heart.

For instance, for treatment of thoracic aortic aneurysms and/or dissections in particular, it is necessary to introduce the stent graft high up in the aorta and in a region of the aortic arch that is curved and where there can be strong blood flow. Furthermore, in the aortic arch there are major branch vessels extending therefrom, such as the brachiocephalic, carotid and/or subclavian arteries. During and/or after treatment of an aneurysm or dissection in the region of the arch, it is desirable for blood supply to continue to flow to these branch arteries. For this purpose, fenestrations or side branches are provided in a stent graft that is placed in that region, through which side arms or branch extensions may be deployed and extend into the brachiocephalic, carotid and/or subclavian arteries, for example.

Custom made graft devices have been used in situations where the arch vessels are compromised and entire coverage of the aortic arch is not required. However, sealing along the aorta wall between the left common carotid and the left subclavian arteries with such graft devices have been problematic. Further, cannulation of these branch arteries through the graft device and deployment of connection devices from the graft devices may be difficult.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION OF THE PREFERRED EMBODIMENTS

Figure 1:
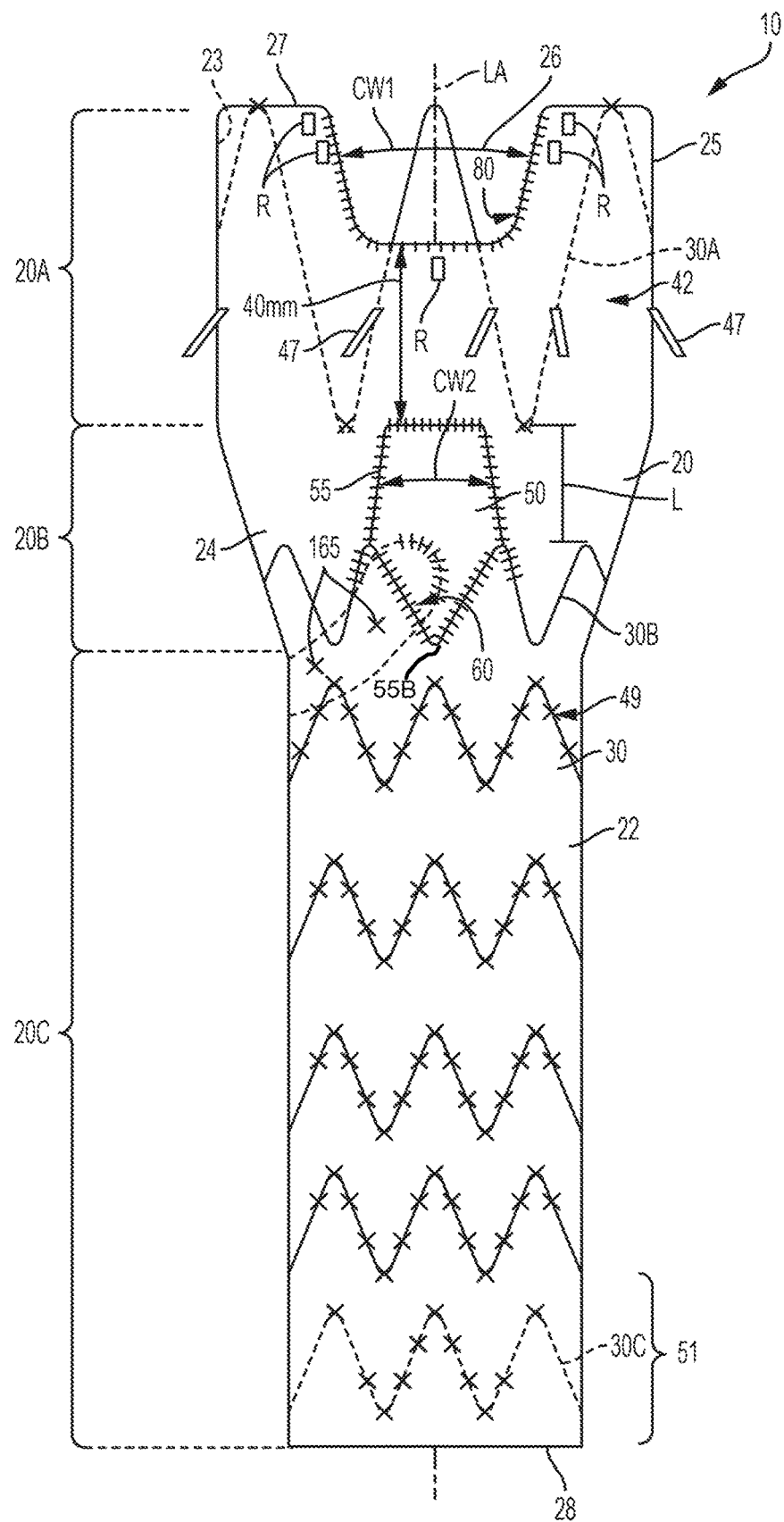
FIG. 1 is a side view of an example of a prosthesis having one example of a trough in communication with a side branch.

Prostheses are disclosed for implantation within a human or animal body for repair of damaged primary vessels, ducts, or other physiological pathways with branch vessels, ducts, or pathways. In a particular example, the prosthesis may be implanted for suitable treatment of diseases of the aorta such as aortic dissection and aortic aneurysm, and in particular, along the aortic arch or descending aorta distal to the subclavian artery. The main body of the prosthesis may be implanted into a primary vessel, and a branch opening or fenestration, such as a trough with side branch and/or scalloped fenestration, may be used to provide cannulation and/or blood perfusion via an internal or external side branch to one or more branch vessels of the primary vessel, such as, for example, the left subclavian artery extending from the aortic arch. The lumen of the side branch may be used as a conduit to implant a connector prosthesis between the side branch and the branch vessel. The prosthesis may be deployed in combination with various other connected prostheses to effectively bridge an aneurysmal and/or dissected portion of the vasculature. Methods of manufacturing the prosthesis are described to facilitate more repeatable and less expensive processes.

The side branch and trough combination disclosed herein may be configured to reduce snagging or otherwise remove impediments to devices (wires, catheters, sheaths, etc.) passing between the main lumen of the prosthesis and the branch lumen of the side branch. The side branch configurations may minimize the time and mental fatigue required to achieve cannulation of such branch vessels. The prostheses described herein with the position and shape of the branch opening and/or scalloped fenestration relative to the prosthesis inflow or proximal end may improve sealing of the prosthesis along a minimal wall of the primary vessel between the intersection of adjacent branch vessels, such as, for example, the subclavian and carotid arteries. When the side branch is placed in a helical configuration, cannulation of the branch vessel may be more easily achieved with the softening of the approach angle between the side branch and the branch vessel, making the transition from axial to radial directions softer. For example, non-helical retrograde configured side branches may be challenging to transition from axial direction to radial direction by the sharp turn. The size of the trough relative to the cross-sectional area of the side branch may make cannulation easier by providing more trough transition space for cannulation. In one example, the positioning of the trough along a taper in combination with the helical retrograde configured side branches may create a larger void between the body vessel wall and the graft wall and the softer transition in which to maneuver and position pass-through devices and connecting stent grafts.

In the present application, the term "proximal" when referring to a prosthesis or a delivery device refers to a direction that is farthest away from an operator using a delivery device, or closest to the aorta, while the term "distal" refers to a direction that is generally closest to the operator using the delivery device, or farthest away from the aorta. Other terms may be used to differentiate the ends, such as an "introduction end" which is intended to be inserted within the patient, and an "operator end" which is that portion of the device that is intended to remain outside of a patient during a procedure. When referring to the prosthesis relative to placement in the human body of the patient, the ends of the various devices and parts of devices may be referred to as the "inflow end" (that end that receives fluid first from the heart), and the "outflow end" (that end from which the fluid exits).

FIG. 1 depicts one example of a prosthesis 10. The prosthesis 10 may include a main graft body 20 formed of a first graft material 22. The graft body includes an inner surface 23 (shown in dashed lines) and an outer surface 24 separated from one another to define a wall thickness of a graft body sidewall 25. The graft body 20 may be shaped and sized to correspond to the vessel to which the graft body is to be implanted. For example, the graft body 20 may be shaped as a generally tubular member having a substantially cylindrical shape, although some axial regions of the graft body 20 may be tapered. In one example, the shape of the graft body 20 may include a proximal section 20A, an intermediate section 20B and a distal section 20C. The intermediate section 20B is disposed between the proximal and distal sections 20A, 20C. The cross-sectional area or diameter of the proximal section 20A may be greater than the cross-sectional area or diameter of the distal section 20C, with the intermediate section 20B tapering inward from the proximal section 20A to the distal section 20C. The inner surface 23 defines a main lumen 26 extending longitudinally within the graft body 20 between a proximal, inflow end 27 and a distal, outflow end 28 thereof along a graft longitudinal axis LA. The main lumen 26 may be suitable for passing a fluid such as, for example, blood therethrough.

At least one support structure, shown as a series of stents 30, is coupled along the graft body 20 between the inflow and outflow ends 27, 28. The stents 30 may move to a radially expanded configuration to have a larger cross-sectional area from a radially compressed configuration when unloaded from the delivery device. The stents 30 coupled to the graft body 20 may exert an outward force on an interior wall of the body vessel, providing support to the body vessel at the point of treatment and to maintain the main lumen 26 of the graft body 20 up to its full cross-sectional area. The support structure may be a single unitary structure or may comprise of a plurality of discrete stents, as shown.

In one example, the support stent structure may comprise of a plurality of discrete stents 30 longitudinally spaced from one another and coupled along the inner surface 23, the outer surface 24, or both of the graft body sidewall 25 via suture attachment ties 49. The stents 30 depicted are shown being defined by a plurality of interconnected unit stent members arranged in an undulating pattern, such as, for example, a zigzag or serpentine pattern. The term "stent" means any device or structure that provides or is configured to provide rigidity, expansion force, or support to a body part, for example, a diseased, damaged, or otherwise compromised body lumen. The stents 30 may include any suitable biocompatible material, including, but not limited to, fabrics, metals, plastics, and the like. Examples of suitable materials include metals such as stainless steel and nitinol, and plastics such as polyethylene terephthalate ("PET"), polytetrafluoroethylene ("PTFE") and polyurethane. The stents 30 may be "expandable," that is, it may be capable of being expanded to a larger-dimension configuration. The stents 30 may expand by virtue of its own resilience (i.e., self-expanding), upon the application of an external force (i.e., balloon-expandable), or by a combination of both. In one example, the stents 30 may have one or more self-expanding portions and one or more balloon-expandable portions. In one example, the stents 30 shown are self-expanding under their inherent resilience. An example of a suitable self-expanding stent includes Z-STENTS™, which are available from Cook Inc., Bloomington, Ind., USA. One or more stents may be made from a woven wire structure, a laser-cut cannula, individual interconnected rings, or another pattern or design.

In one example, a discrete first proximal stent 30A that is in close proximity to the inflow end 27 of the graft body 20 may be disposed along the inner surface 23 to define an outer proximal annular bare region 42. The outer proximal annular bare region 42 along the outer surface 24 of the graft body 20 extends between the inflow end 27 of the graft body 20 and the axial length of the first proximal stent 30A so that the exterior graft does not include a support stent structure. The length of the outer proximal annular bare region 42 may correspond to the length of the proximal section 30A.

A discrete second proximal stent 30B may be positioned distal to the first proximal stent 30A. The second proximal stent 30B is shown disposed along the tapered intermediate section 20B, and may be disposed along the distal end of the tapered intermediate section 20B. The second proximal stent 30B may be disposed on the inner surface 23 or along the outer surface 24 (as shown). In one example, one side of the sidewall of the tapered intermediate section 20B may vary in radii along its length, and the opposite side of the sidewall of the tapered intermediate section 20B may have a constant radii along its length. The tapered intermediate section may provide additional spacing between the sidewall and the vessel wall for making cannulation easier.

The first and second proximal stents 30A, 30B may have a series of respective proximal apices and distal apices. The relative position of the first and second proximal stents 30a, 30b may be arranged in a peak-to-peak arrangement where the distal apices of the first proximal stent are in alignment with the proximal apices of the second proximal stent. Alternatively, the relative position of the first and second proximal stents 30a, 30b may be arranged in a peak-to-valley arrangement the distal apices of the first proximal stent are in alignment with the distal apices of the second proximal stent. The remaining stents along the distal section 20C may be arranged in a peak-to-peak arrangement with each other, where the proximal apices are in alignment with other proximal apices. The proximal-most stent of the remaining stents 30 may be arranged in a peak-to-valley arrangement with the second proximal stent 30B. Other stent arrangements are contemplated.

A discrete distal stent 30C that is in close proximity to the outflow end 28 of the graft body 20 is also illustrated, and may be disposed externally or internally to the graft body. In one example, the distal stent 30C may be disposed along the inner surface 23 to define an annular distal bare region 51 extending proximally between the outflow end 28 and the first external stent. The outer annular proximal bare region 42 and/or the annular distal bare region 51 along the outer surface 24 of the graft body 20 may not include a support stent structure ("unstented"), but may include barb or anchoring structures 47. In other words, each of the annular bare regions 42, 51 may provide the prosthesis 10 an unobstructed sealing zone to be placed apposed to the walls of the body vessel.

The first proximal stent 30A and the second proximal stent 30B may be spaced longitudinally from one another by a distance L (for example, between distal apices of the first proximal stent and proximal apices of the second proximal stent) of between about 2 mm and about 20 mm, typically between about 5 mm and about 13 mm. In one example, the spacing between the first proximal stent 30A and the second proximal stent 30B may vary circumferentially around the graft body 20. The spacing between other portions of the support stent structure (for example, between other adjacent stents 30) may be similar to the spacing between the first proximal stent 30A and the second proximal stent 30B. In other examples, adjacent stents may be spaced any suitable distance from one another. The spacing between the adjacent stents may be sufficiently large to enable such flexibility of the graft body. In other words, an unsupported longitudinal section of the graft material of the graft body 20 between the adjacent stents may be sufficiently flexible to enable movement of the graft body. The stent sizing, spacing, and design may be determined so that there is no stent-to-stent contact even in tortuous anatomy. Stents preferably may be placed to maximize prosthesis flexibility while maintaining patency, as well as reducing material wear and stent fatigue.

Figure 2:
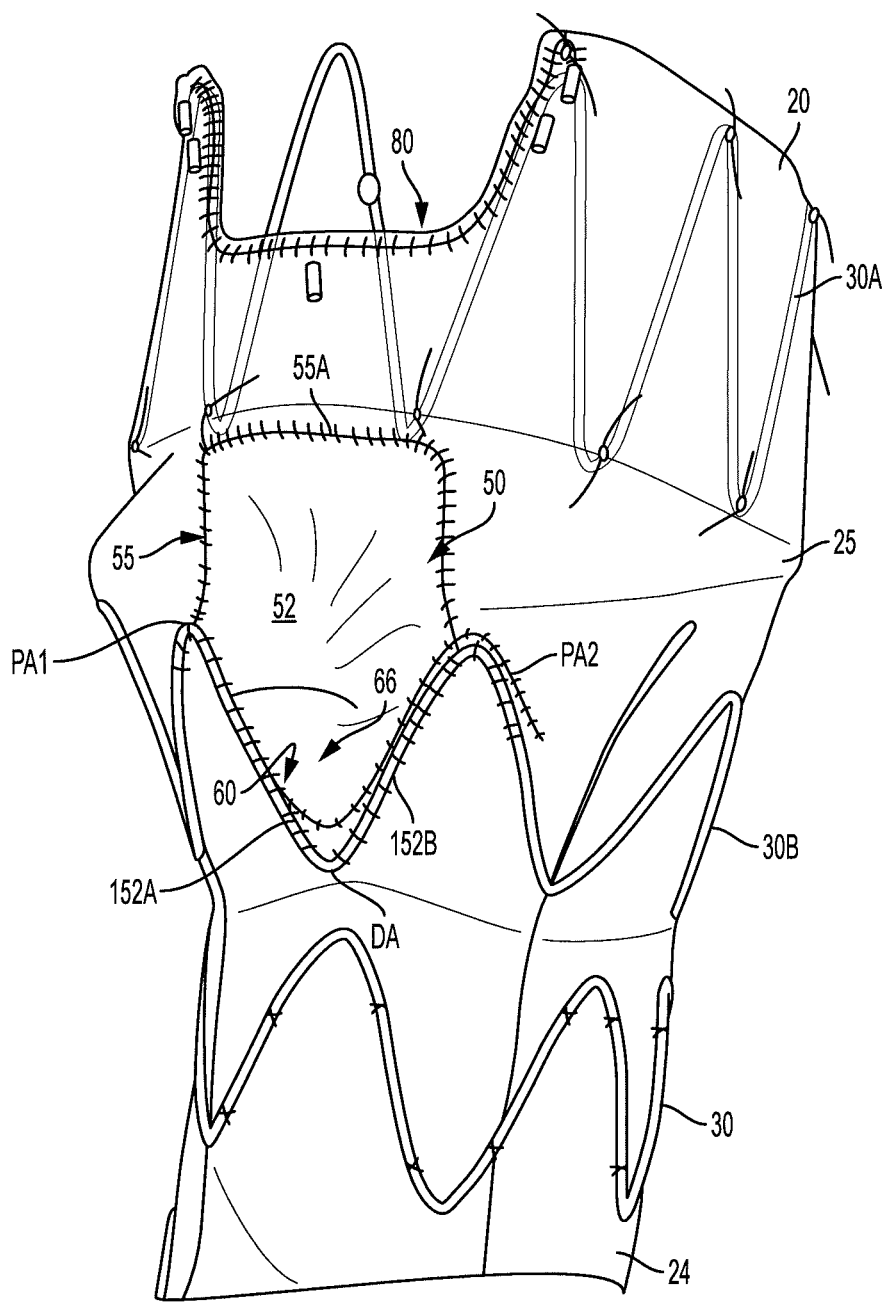
FIG. 2 is a perspective partial view of the trough and the side branch of the prosthesis depicted in FIG. 1.

With additional reference to FIG. 2, the graft body 20 includes a branch opening or trough 50 formed in the graft body 20 leading to a side graft branch 60. The trough may be located along any portion of the graft body. The trough 50 and the side branch 60 may be positioned generally within the main lumen 26 of the graft body. The trough 50 may be defined by a trough wall 52 extending between the outer surface 24 of the sidewall 25 and the side branch 60. The trough 50 and the side branch 60 together define a transport conduit for devices or body fluid. The trough 50 may be further defined by a trough boundary 55 formed at the sidewall 25 along the outer surface 24 of the graft body 20. The trough boundary 55 includes a proximal axial side 55A and a distal axial side 55B, where the proximal axial side 55A is in closer proximity to the inflow end 27 than the distal axial side 55B. Further, the trough 50 of any one of the disclosed prostheses may be positioned near the inflow end of the graft body. For example, the trough may be placed between about 5 mm and about 30 mm, between about 10 mm and about 25 mm, or between about 15 mm and about 20 mm from the inflow end of the graft body.

The side branch 60 includes an inner surface and an outer surface. The side branch 60 may be configured as a generally tubular member. The inner surface of the side branch defines a branch lumen 66 extending longitudinally within the side branch 60 between a pair of ends thereof. In one example, the trough 50 is coextensive with the branch lumen 66 to define the conduit. The trough 50 and the branch lumen 66 may be in fluid communication with each other and with the main lumen 26 of the graft body 20. The side branch 60 is shown in the figures as an internal side branch, although an external side branch is contemplated and may be configured in a similar fashion as that of the internal branch with the trough extending radially outward. Further, the orientation of the side branch may be in the antegrade or retrograde configuration or other positions, as further described.

Figure 3:
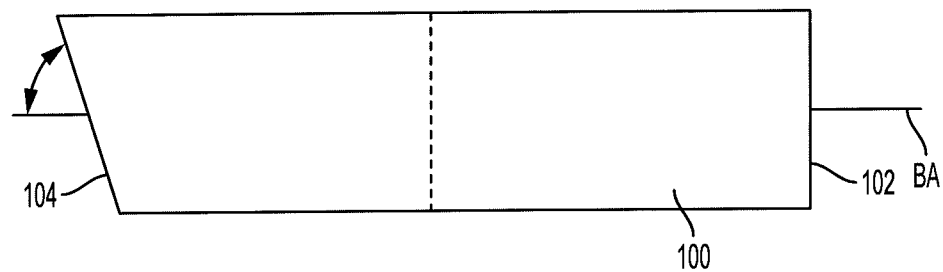
FIGS. 3-5 depict an example of forming a trough wall and a side branch from the same material for the prosthesis depicted in FIG. 1.
Figure 4:
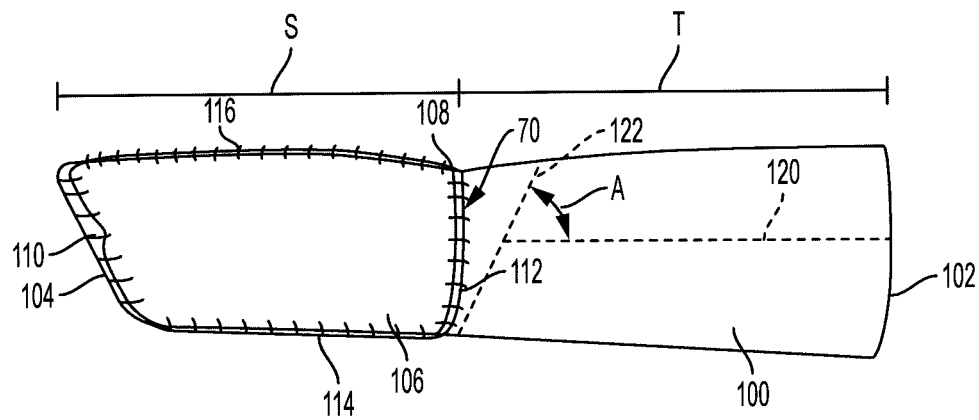
Figure 5:
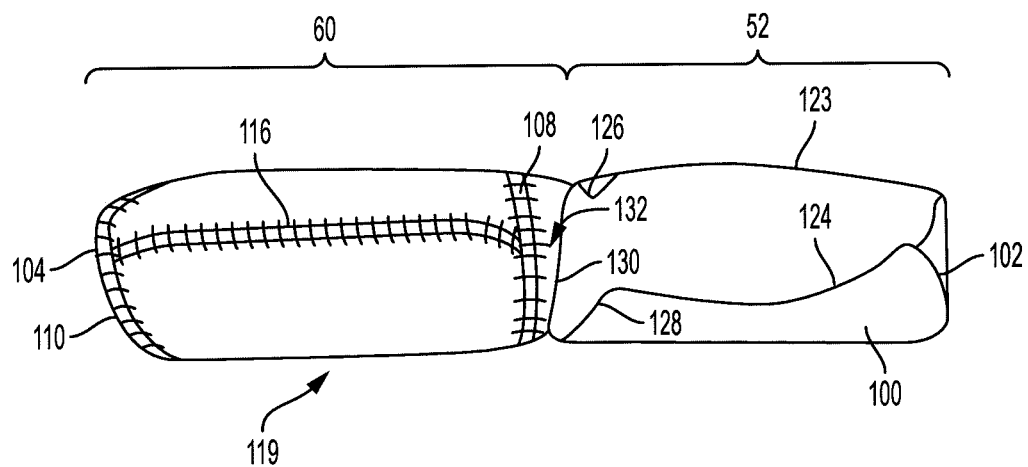

The trough wall 52 forming the trough 50 and the side branch 60 may comprise of one or more of the graft materials described below. As shown in FIGS. 3-5, a second graft material of the trough wall 52 may be formed integrally with a third graft material of the side branch 60. Alternatively, the second graft material forming the trough wall may be separate for attachment to the third graft material forming the side branch to achieve the configuration shown in FIG. 3.

FIG. 3 depicts the third graft material 100 used to make the side branch 60. The third graft material 100 may be formed into a tube, such as, for example, formed from a sheet of graft material where axial edges are rolled and attached with stitching with suture or other biocompatible thread, or adhesives, or woven or otherwise formed directly into a tube of graft material. The size of the third graft material 100 is selected for its intended purpose, such as, in one example, about 55-60 mm. The edges of the third graft material may be squared and/or beveled. In one example, a first edge 102 of the third graft material 100 may be squared off or otherwise made substantially orthogonal to a branch axis BA, about which the side branch is disposed. A second edge 104 of the third graft material 100 may be beveled or otherwise made oblique relative to the branch axis BA.

The side branch 60 formed by the third graft material 100 may include at least one branch support structure 70 to aid at least in maintaining the branch lumen 66 open and/or in biasing the side branch in a specific configuration. In FIG. 4, the side branch 60 includes at least one branch support structure 70, which may include a single, unitary structure or a plurality of independent structures. The side branch support structure 70 and/or various portions thereof may be disposed on an inner surface and/or an outer surface 106 (shown) of the third graft material 100 along the region of the graft material for forming the side branch 60. The outer surface 106 defines the outer surface of the side branch 60, while the inner surface of the graft material 100 defines the inner surface of the side branch 60, which defines the branch lumen 66.

Multiple branch support structures 70 may be positioned at any points along a length S of the third graft material 100 for forming the side branch 60. The support structure 70 may extend between the second edge 104 and an intermediate location 108. The length S defines generally the size of the side branch 60 that is to be inserted within the main graft, and in one example, is about 26 mm for a 55-60 mm length graft material. In one example, the side branch support structure 70 may be configured as a helical stent extending generally longitudinally and circumferentially along the side branch 60. The side branch support structure 70 also may be configured as one or more annular rings positioned along the length of the side branch 60. Alternatively, or additionally, any other type of stent including, for example, those described above in reference to the support stent structure or stent 30 may be used. The side branch support structure 70 may be formed from any material known in the art including, for example, the materials described above with reference to the support stent structure or stent 30.

In one example, the side branch support structure 70 may include one or more of the following. A ring support may be disposed about one of or both of the second edge 104 of the graft material. One or more axial struts circumferentially spaced from one another along the tubular graft material may also be provided. In one example, the side branch support structure 70 is defined by a first ring 110 coupled along the second edge 104 with suture stitching. Because of the angled end of the second edge 104, the first ring 110 is similarly disposed along the same angle as the second edge 104. A second ring 112 may be coupled about the intermediate location 108 with suture stitching. The second ring 112 may be disposed generally orthogonal to the branch axis BA. A first longitudinal strut 114 is shown extending between the first ring 110 and the second ring 112, and coupled to the third graft material 100 with suture stitching. A second longitudinal strut 116 is shown extending between the first ring 110 and the second ring 112, and coupled to the third graft material 100 with suture stitching. The second longitudinal strut 116 is circumferentially spaced from the first longitudinal strut 114, for example, by about 180 degrees. The second longitudinal strut 116 may be bowed or have an outward curvature. Any two or more the rings and the longitudinal struts of the side branch support structure 70 may be integrally formed into a single unit. In one example, the first longitudinal strut 114 and the second ring 112 is a single structure prior to attachment to the graft material. For instance, an end of the first longitudinal strut 114 may be welded or bonded to a face of the second ring 112.

The remaining portion T of the third graft material 100 is configured to form the trough wall 52 such that the second graft material and the third graft material may be integrally formed from a common same graft material. The third graft material 100 may be sized and shaped to define a trough-branch unit 119. The remaining portion T generally extends from the intermediate location 108 to the first edge 102 of the third graft material 100. FIG. 4 illustrates a series of cut lines 120, 122 (shown in dashed lines) that may be used when the graft material is cut for forming the trough wall. The first cut line 120 is shown extending longitudinally from the first edge 102 to just short of the second ring 112, and may be extend along the branch axis BA. Another cut line circumferentially disposed from the first cut line 120 may be used to remove a greater portion of graft material. The second cut line 122 is shown extending partially circumferentially. In an example, the second cut line 122 transverses the end of the first cut line 120. In one example, the second cut line 122 is obliquely angled at angle A relative to the first cut line 120 and the branch axis.

FIG. 5 illustrates the trough-branch unit 119 formed from the third graft material 100 after being cut along the cut lines 120, 122 shown in FIG. 4. The cutting operation may be performed by scissors, scalpel or sharp blade, punched out, or laser or other non-blade cutting systems. The remaining portion T is shown unfurled and now defined by the first edge 102 of the graft material 100, a pair of longitudinal edges 123, 124 formed by the first cut line 120, and a pair of flap edges 126, 128 opposite the first edge 102 formed by the second cut line 122. A partial branch edge 130 is also formed by the second cut line 122 and is shown extending at the same oblique angle A of the second cut line. The branch edge 130 may be longitudinally spaced from the second ring 112 to define a circumferential segment 132 of graft material that is beyond the second ring.

Depending on the use and orientation of the side branch 60 relative to the graft body 20, that is, where devices or fluid flow may enter one end or the other end of the side branch, in one example, the second edge 104 may be referred to as the inlet, distal end of the side branch 60, and the partial branch edge 130 at least partially coupled to the trough wall 52 may be referred to as the outlet, proximal end of the side branch 60. In another example, the second edge 104 may be referred to as the outlet end of the side branch 60, and the partial branch edge 130 may be referred to as the inlet end of the side branch 60.

Figure 8:
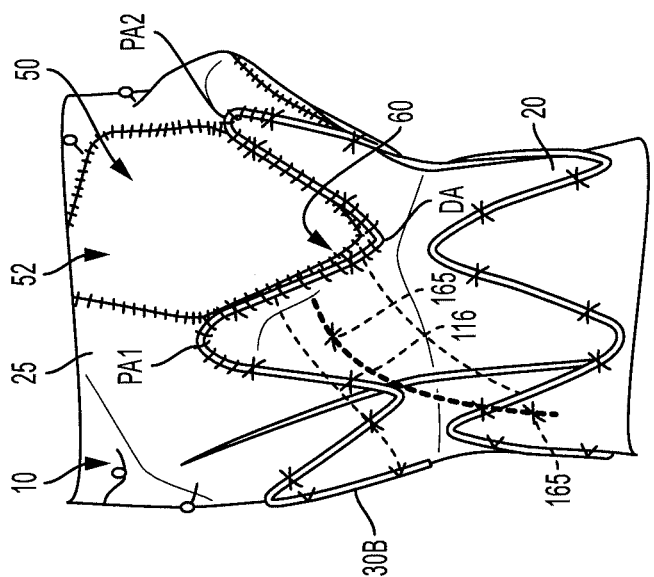
FIGS. 6-8 depict attachment of a trough wall to a graft body of the prosthesis depicted in FIG. 1.
Figure 7:
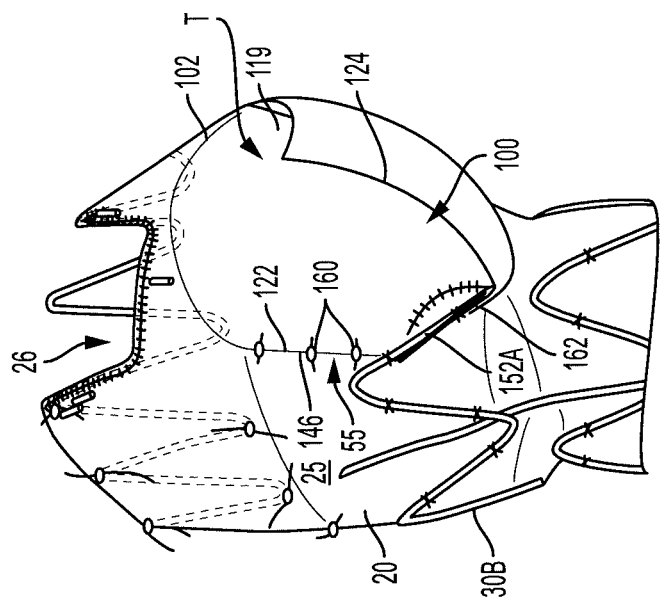
Figure 6:
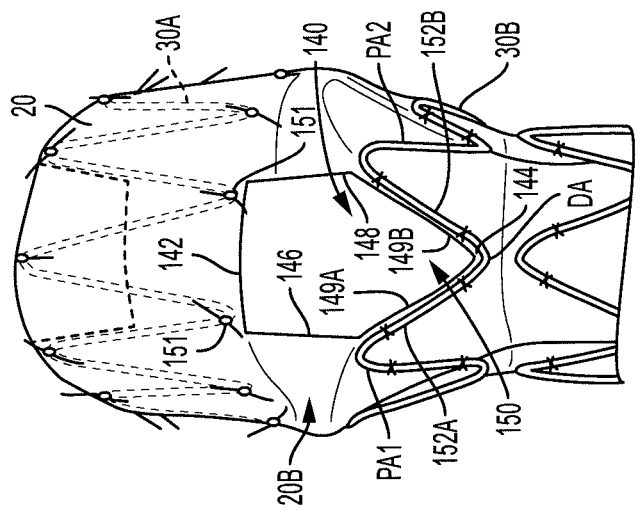

FIGS. 6-8 illustrate the attachment of the side branch 60 configured from the third graft material 100 to the graft body 20 sized accordingly to meet the size of the patient's anatomy. Although the graft body 20 is shown with the stents already coupled, the following step may occur prior to coupling of the stents. FIG. 6 shows a cutout 140 formed in the graft body 20 between the locations of the first proximal stent 30A and the second proximal stent 30B. The cutting operation may be performed by scissors, scalpel or sharp blade, punched out, or laser or other non-blade cutting systems. When the intermediate section is tapered, the cutout 140 may be formed along the tapered intermediate section 20B, as shown. The cutout 140 may define the trough boundary 55 formed at the sidewall of the graft body 20.

The cutout 140 may have various shapes. In one example, the cutout 140 may be a multi-sided (shown with five sides) shaped cutout defined by cutout edges 142, 146, 148, 149A, 149B. The first cutout edge 142 is shown defining the proximal axial end of the cutout 140, and extends partially circumferentially. The first cutout edge 142 may be extended circumferentially along a pair of adjacent distal apices 151 of the first proximal stent 30A. The second and third cutout edges 146, 148 may extend longitudinally in the distal direction from opposite ends of the first cutout edge 142. The second and third cutout edges 146, 148 may be parallel to one another and/or may extend orthogonal to the first cutout edge 142. The second and third cutout edges 146, 148 are shown extending distally to a location short of adjacent proximal apices PA1, PA2 of the second proximal stent 30B. The fourth and fifth cutout edges 149A, 149B extend longitudinally in the distal direction from the respective ends of the second and third cutout edges 146, 148. The fourth and fifth cutout edges 149A, 149B are shown extending converging to a corner point 144 disposed at one of the distal apices DA of the second proximal stent 30B to form an inward tapered portion 150 of the cutout 140. The corner point 144 may be positioned approximately at the lateral center of the first cutout edge 142. The shape of the tapered portion 150 may correspond to the angular shape defined by the pair of adjacent interconnected stent members 152A, 152B forming the distal apex DA of the second proximal stent 30B.

FIG. 7 illustrates the attachment step of a trough portion of the trough-branch unit 119 of the third graft material 100 to the graft body 20 via stitching using a running blanket stitch configuration. The trough or trough walls may be coupled by an attachment to the graft body and/or to the support stent structure by any suitable method. For example, the coupling attachment between the graft materials and stent structure may be achieved by suture stitching, wire, staples, clips, bonding agents, or other methods that may be used to achieve a secure attachment. The coupling between the components may form a fluid-tight seal, including using a sealant or adhesive, along or in combination with another coupling mechanism such as stitching, to enhance the seal.

In one example, the length S of the graft material defining the side branch 60 is inserted within the cutout 140 and disposed within the main lumen 26. The longitudinal edge 123 of the graft material is attached to the sidewall 25 of the graft body 20 by suture stitches. In one example, a plurality of stitches 160 are used to initially fix the position of the remaining portion T of the graft material along the cutout edges, such as for example, cutout edges 142, 146, 148, 149A, 149B. In one example, a portion of the longitudinal edges 123, 124 may also be stitched at least partially along the adjacent interconnected stent members 152A, 152B of the second proximal stent 30B. To this end, the stent members 152A, 152B may form an aspect of a trough frame 162. The trough frame may add structural support to the trough boundary. The trough frame may be a flexible frame formed from any material described above with reference to the support stent structure or stent. Once the position of the remaining portion T of the graft material is fixed, the trough boundary 55 may be further stitched with blanket stitching. The remaining portion T is sized larger than the area of the cutout 140, and when attached, the excess of the remaining portion T is positioned inward beyond the sidewall to form the trough wall 52 extending radially inward from the sidewall 25 of the graft body 20. The blanket stitching may also be applied along the proximal apices PA1, PA2 of the second proximal stent 30B to securely attach the proximal apices PA1, PA2 to the sidewall 25 if the graft body 20 and reinforce the trough boundary at that region.

FIG. 8 illustrates the prosthesis 10 in a final form with the side branch 60 and the trough wall 52 attached to the graft body 20. The side branch 60 is positioned in a retrograde configuration such that the second edge 104 is positioned closer to the outflow end 28 than to the trough 50. The side branch 60 may be placed in a helical configuration along the inner surface 23 of the sidewall 25, being disposed longitudinally and circumferentially. Suture stitches 165 may be utilized to fix the side branch in the helical configuration. The second longitudinal strut 116, shown in dashed lines in FIG. 8, shows the curvature and the helical positioning of the side branch.

Figure 9:
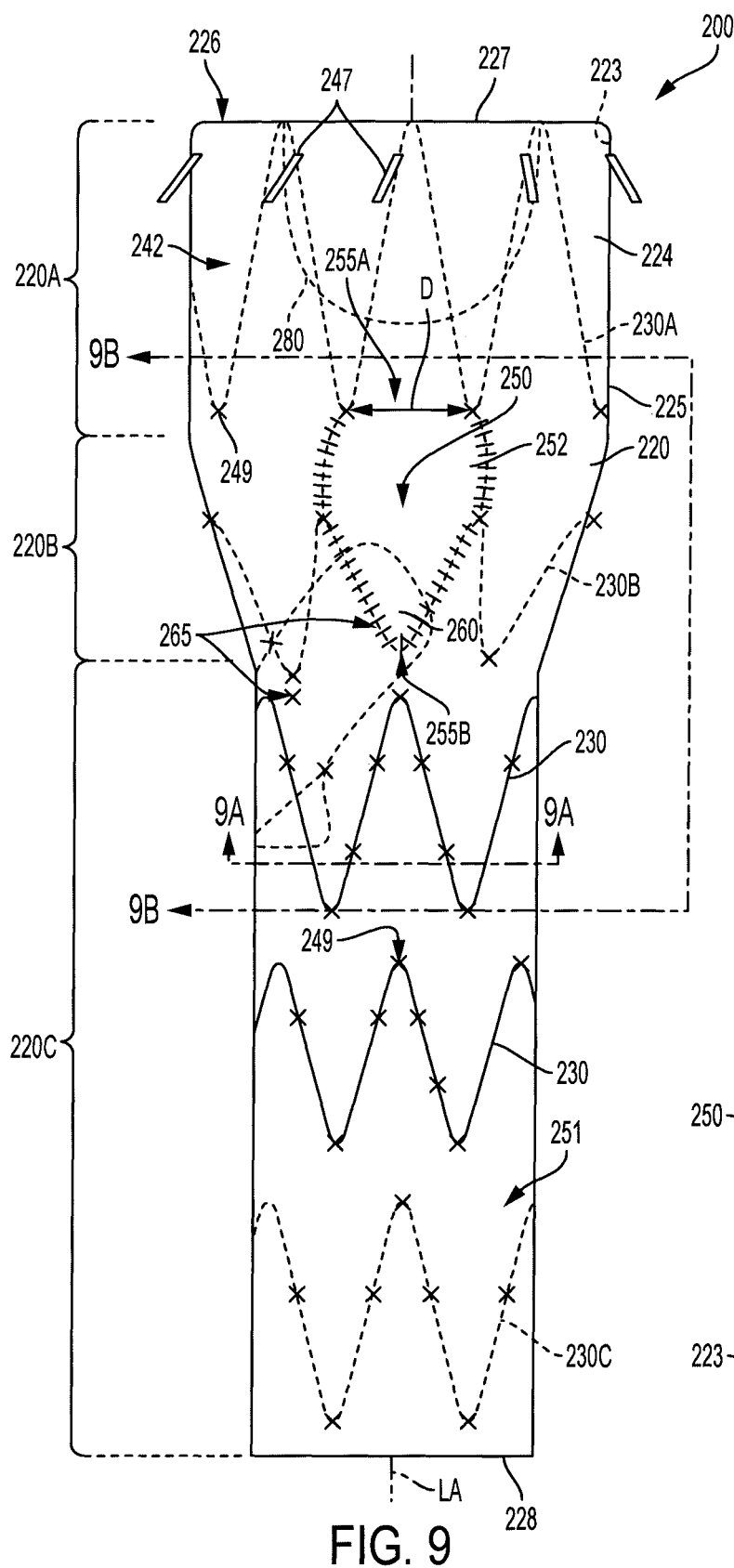
FIG. 9 is a side view of another example of a prosthesis having one example of a trough in communication with a side branch.

FIG. 9 depicts another example of a prosthesis (now referred to as prosthesis 200), having similar features as the prosthesis 10 disclosed herein and thus similar terms will be used in the description of the prosthesis 200. The tubular graft body 220 may include one of the disclosed graft materials disclosed below, and may be shaped and sized to correspond to the vessel to which the graft body is to be implanted. The graft body 220 may be substantially cylindrical shape, although some axial regions of the graft body 220 may be tapered. As shown, the cross-sectional area or diameter of the proximal section 220A may be greater than the cross-sectional area or diameter of the distal section 220C, with the intermediate section 220B tapering inward from the proximal section 220A to the distal section 220C. The main lumen 226 extends longitudinally within the graft body 220 between the inflow end 227 and the outflow end 228 along the longitudinal axis LA.

At least one support structure, shown as discrete stents 230, is coupled along the graft body 220 between the inflow and outflow ends 227, 228. The spacing between adjacent stents may provide the flexibility and open patency as described above. The stents 230 may be longitudinally spaced from one another and coupled along the inner surface 223, the outer surface 224, or both of the graft body sidewall 225 via suture attachment ties 249. The stents 230 may include the configuration and the materials disclosed above. The first proximal stent 230A is in close proximity to the inflow end 227 of the graft body 220, and may be disposed along the inner surface 223 of the graft material to define the outer proximal annular bare region 242. The discrete second proximal stent 230B may be positioned distal to the first proximal stent 230A. The second proximal stent 230B is shown disposed along the tapered intermediate section 220B. The second proximal stent 230B may be disposed on the inner surface 223 (as shown) or along the outer surface 224. The relative position of the first and second proximal stents 230A, 230B may be arranged in a peak-to-peak arrangement, as shown, or in a peak-to-valley arrangement. The remaining stents along the distal section 220C may be arranged in a peak-to-peak arrangement with each other. The proximal-most stent of the remaining stents may be arranged in a peak-to-valley arrangement with the second proximal stent 230B. Other stent arrangements are contemplated.

The discrete distal stent 230C is in close proximity to the outflow end 228 of the graft body 220, and may be disposed externally or internally to the graft body. In one example, the distal stent 230C may be disposed along the inner surface 223 of the graft material to define an annular distal bare region 251 extending proximally between the outflow end 228 and the first external stent. The outer proximal annular bare region and/or the outer distal annular bare region along the outer surface of the graft body 220 may provide unobstructed sealing zones and may also include barb or anchoring structures as shown.

Figure 10:
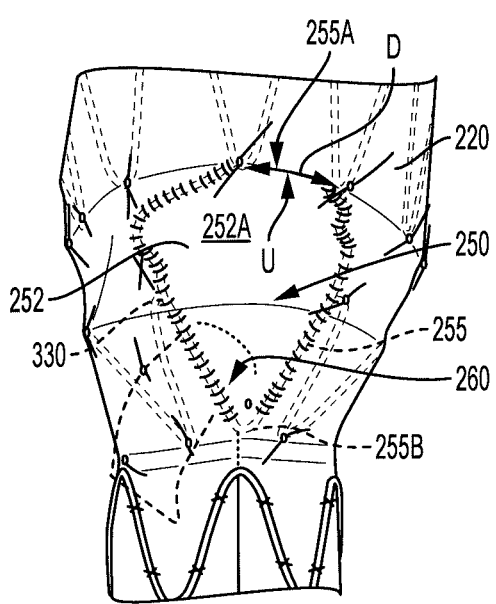
FIG. 10 depicts a partial view of the trough and the side branch of the prosthesis depicted in FIG. 9.

With additional reference to FIG. 10, the trough 250 is a branch opening formed in the graft body 220 that leads to the side branch 260 positioned generally within the main lumen 226 of the graft body 220. The trough wall 252 extends between the outer surface 224 of the sidewall 225 and the side branch 260 such that the trough 250 and the side branch 260 together define the transport conduit for devices or body fluid. The boundary 255 of the trough 250 may include the proximal axial side 255A and the distal axial side 255B.

Figure 11:
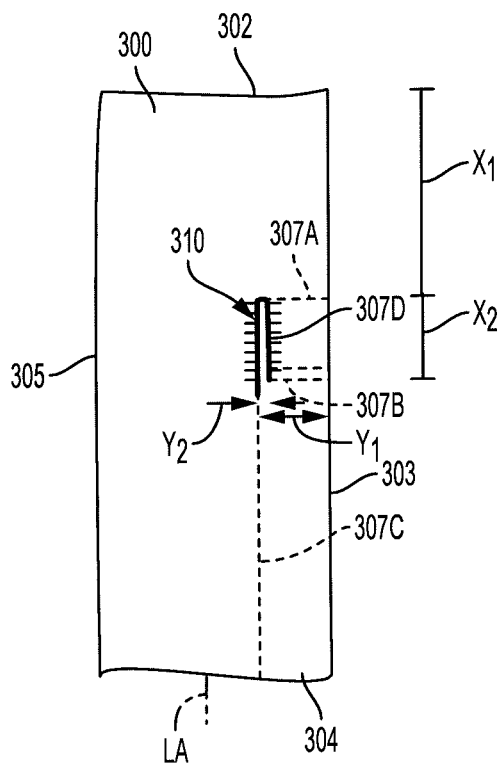
FIGS. 11-14 depict formation of a trough, a side branch, and a graft body of the prosthesis depicted in FIG. 1 from the same material.

FIGS. 11-17 illustrate the trough wall 252, the side branch 260, and the graft body 220 formed as an integrated unit of a same common graft material. FIG. 11 depicts the graft material 300 formed into a tube, such as, for example, formed from a sheet of graft material where axial edges are rolled and attached with suture stitching or adhesives, or woven or otherwise formed directly into a tube of graft material. The size of the graft material is selected to meet the size of the patient's anatomy. The first axial edge 302 and the second axial edge 304 of the graft material 300 may be squared off or otherwise made substantially orthogonal to the longitudinal axis LA. The first side edge 303 and the second side edge 305 form the edges of the graft material 300. The distance between the first and second side edges 303, 305 may correspond to the desired diameter of the proximal section 220A of the graft body 220. The distance between the first and second axial edges 302, 304 may correspond to the desired overall length of the graft body 220.

Lines are shown marked on the graft material 300 to indicate the position of the side branch relative to the graft body. In one example, a first transverse line 307A is marked extending from the first side edge 303. The first transverse line may be generally orthogonal to the longitudinal axis LA and longitudinally spaced from the first axial edge 302 by a distance X1. The distance X1 may correspond generally to the desired length of the outer proximal annular bare region 242. A second transverse line 307B is marked extending from the first side edge 303. The second transverse line 307B may be generally orthogonal to the longitudinal axis LA and longitudinally spaced from the first transverse line 307A by a distance X2. The distance X2 may correspond generally to the desired length of the side branch 260. The first and second transverse lines 307A, 307B may be in a parallel relationship. A first longitudinal line 307C is marked extending from the second axial edge 304. The first longitudinal line 307C may be generally parallel to the longitudinal axis LA and laterally spaced from the first side edge 303 by a distance Y1. The first longitudinal line 307C may intersect the end of the first transverse line 307A. The difference between the overall diameter of the graft material and the distance Y1 may correspond to the desired diameter of the distal section 220C of the graft body 220. A second longitudinal line 307D is marked extending proximally from the end of the second transverse line 307B and generally parallel to the longitudinal axis LA. The second longitudinal line 307D may be laterally spaced outwardly toward the first side edge 303 from and in a parallel relationship to the first longitudinal line 307C by a gap distance Y2. The first longitudinal line 307C may intersect the first transverse line 307A. The difference between distances Y1, Y2 may correspond to the desired diameter of the side branch 260.

The lines marked include a prosthesis configuration with an inflow segment greater in diameter than the outflow segment with the trough positioned along a tapered section. In other examples, the various lines may be positioned accordingly to achieve other configurations, such as, for example, the diameters of the inflow end segment and the outflow end segment being substantially equal with the trough positioned along a tapered section or nontapered section. Here, the first longitudinal line 307C may angle or curve outward to the first side edge 303 at a point beyond the end of the second longitudinal line 307D such that the resulting first and second diameter section 311A, 311B would be substantially equal. In another embodiment, another line (not shown) may be used to cut a segment such that the common tubular section 309C of the graft material bounded by the edge 302 and the dashed line extending along the line 307A would have a diameter substantially equal to the diameter represented by the line 307C in FIG. 11.

As shown in FIG. 11, blanket stitching 310 may be applied along the second longitudinal line 307D. The blanket stitching may start at the intersection between the longitudinal line 307D and the second transverse line 307B and proximally up to the first transverse line 307A. The blanket stitching may continue along a small circumferential portion of the first transverse line 307A by the distance Y2 toward the intersection of the first transverse line 307A and the first longitudinal line 307C. The blanket stitching may continue along the first longitudinal line 307C distally down toward the second axial edge 304 by a distance of at least up to the distance X2. Attachment of the graft material 300 to itself along the remaining portion of the first longitudinal line 307C may be performed by stitching and/or a biosealant or bioadhesive.

Figure 12:
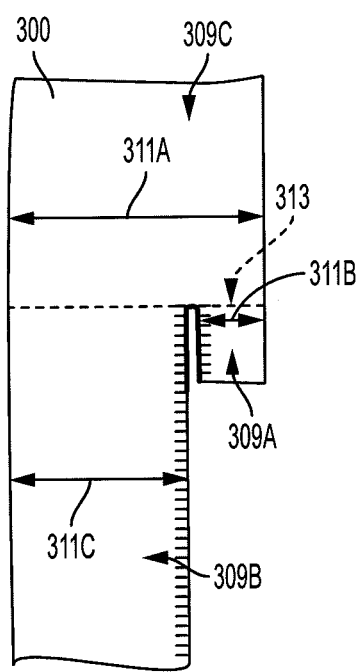
Figures 14, 15, 16:
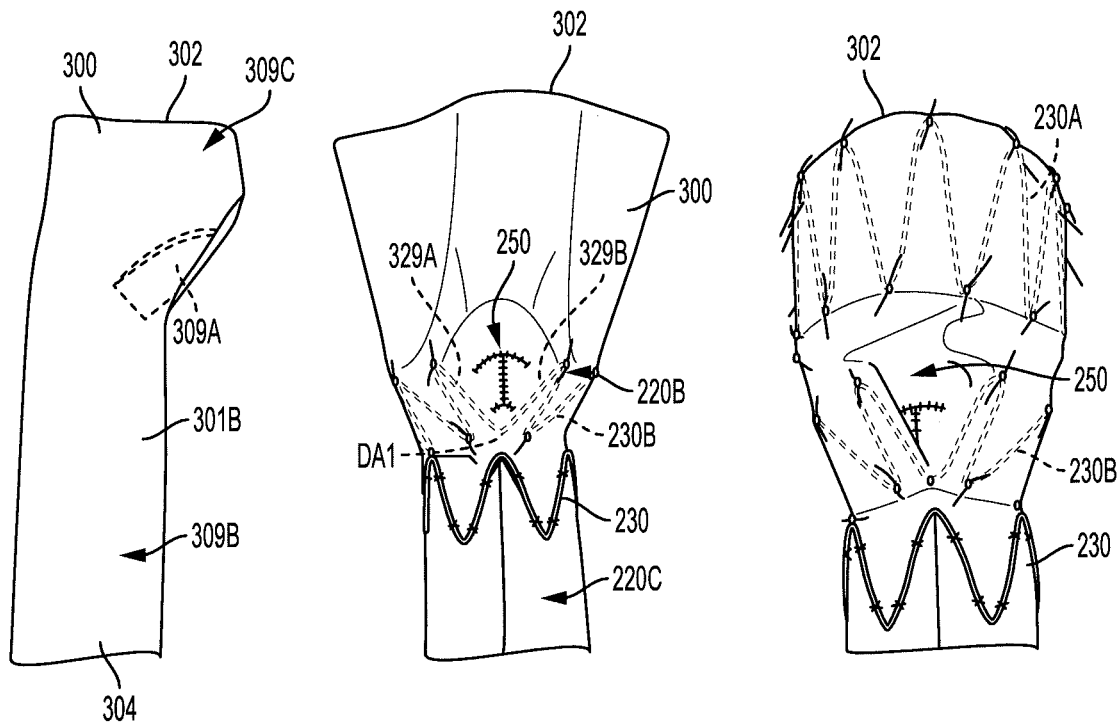
FIGS. 15-17 depict further steps to forming the prosthesis depicted in FIG. 9.

In FIG. 12, portions of excess graft material is removed. For example, the graft material 300 may be cut along the first longitudinal line 307C, along the second transverse line 307B and the region between first and second longitudinal lines 307C, 307D. The cutting may be slightly outside of line. The cutting operation may be performed by scissors, scalpel or sharp blade, punched out, or laser or other non-blade cutting systems. Stitching made be added along the cut along line 307C to form a tubular section. This results in the overall shape and size for forming the side branch and the main graft body, with a first leg 309A associated with the side branch 260 and a second leg 309B associated with the main graft body 220 in a bifurcated relationship. The second leg 309B is shown having a greater length and width than the first leg 309A. The first leg 309A and the second leg 309B are tubular and shown extending from a common tubular section 309C of the graft material bounded by the edge 302 and the dashed line extending along the line 307A. The common section 309C defines a first diameter section 311A. The first leg 309A defines a second diameter section 311B associated with the diameter of the side branch, and the second leg 309B defines a third diameter 311C associated with the diameter of distal section of the main body. The second diameter section 311B is smaller than the first diameter section 311A. The second diameter section 311B may be smaller than the third diameter section 311C. The transition (shown generally by arrow 313) between the first leg 309A and the common section 309C may define at least an aspect of the trough wall disposed along the tapered intermediate section that interconnects the first diameter and second diameter sections, as shown in FIG. 14. Instead of removing portions such as shown in FIGS. 11-12, the graft material may be formed, such as by weaving, knitting, sewing or other textile processes, having the shape in FIG. 12.

Figure 13:
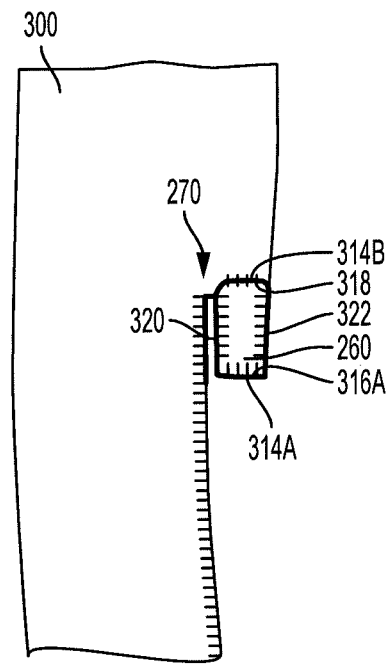

In FIG. 13, the side branch support structure 270 may be configured as has been disclosed previously. In one example, the side branch support structure 270 may include one or more of the following. First ring support 314A may be disposed, for example, by stitching, about the edge 316A of the second leg 309A of the graft material. The edge 316A may define one of the ends of the side branch 260. Second ring support 314B may be disposed, for example, by stitching, about the intermediate location 318 at the transition between the first and second legs. The intermediate location 318 may define an aspect of the opposite end of the side branch 260 to be formed. The edge 316A or location 318 may be angled, and the ring supports may be similarly disposed along the same angle. One or more axial struts circumferentially spaced from one another along the tubular graft material may also be provided. The first longitudinal strut 320 is shown extending between the first ring 314A and the second ring 314B, and coupled to the first leg 309A with blanket stitching. The second longitudinal strut 322 is shown extending between the first ring 314A and the second ring 314B, and coupled to the first leg 309A with blanket stitching. The second longitudinal strut 322 is circumferentially spaced from the first longitudinal strut 320, for example, by about 180 degrees. Any one of the longitudinal struts may be bowed or have an outward curvature. Any two or more the ring supports and the longitudinal struts of the side branch support structure 270 may be integrally formed into a single unit. In one example, the first longitudinal strut 320 and the second ring 314B are a single structure prior to attachment to the graft material, and similarly for the second longitudinal strut 322 and the first ring 314A. For instance, an end of the longitudinal strut may be welded or bonded to a face of the corresponding rings.

In FIG. 14, the first leg 309A associated with the side branch 260 is inverted and placed within the second leg 309B of the main lumen 226 of the graft body. In one example, the tubular common graft material 300 without the first and second legs 309A, 309B may be everted such that the inner surface faces outward. After the lines are marked and the cutting and stitching forming of legs 309A, 309B, the graft material 300 may be everted such that the outer surface faces outward which achieves the inversion of the side branch. In one example, the trough and the side branch are in an inverted relationship relative to the main body. In FIG. 15, the second proximal stent 230B is coupled to the graft material 300 forming the graft body 220 by, for example, by a plurality of suture stitches. In one example, the second proximal stent 230B is shown disposed along the inner surface of the tapered intermediate section 220B. The interconnected stent members of the second proximal stent 230B are configured to take on the shape of the tapered intermediate section. The pair of adjacent interconnected stent members 329A, 329B of the second proximal stent 230B that form the distal apex DA1 may be located around the trough 250. For example, the distal apex DA1 may be centrally located about the distal base of the trough boundary 255 and at the transition of the tapered intermediate section 220B and the distal section 220C. The trough 250 is at least partially disposed along the tapered intermediate section 220B which may provide more clearance space for passing devices. One of the remaining stents 230 may be coupled to the outer surface of the distal section 220C of the graft body 220 by, for example, by a plurality of suture stitches, distal to the second proximal stent 230B. The first stent 230 may be positioned in a peak-to-peak relationship with the second proximal stent 230B.

In FIG. 16, additional stents are added to the graft material. For example, additional stents 230 may be coupled to the outer surface of the distal section 220C of the graft body 220 by, for example, at a plurality of suture stitching locations distal to the first stent 230. These additional stents 230 may be positioned in a peak-to-valley relationship with the other stents 230. The distal stent 230C may be disposed along the inner surface of the graft material to define the annular distal bare region. The first proximal stent 230A may be coupled in close proximity to the first axial edge 302 of the graft material 300 and proximal to the second proximal stent 230B at a plurality of suture stitching locations. The first proximal stent 230A may be disposed along the inner surface of the graft material to define the outer proximal annular bare region. The first axial edge 302 is shown to correspond to the inflow end 227 of the graft body 220. The second axial edge 304 corresponds to the outflow end 229 of the graft body. The first proximal stent 230A may be positioned in a peak-to-valley relationship with the second proximal stent 230B.

Figures 17, 17A:
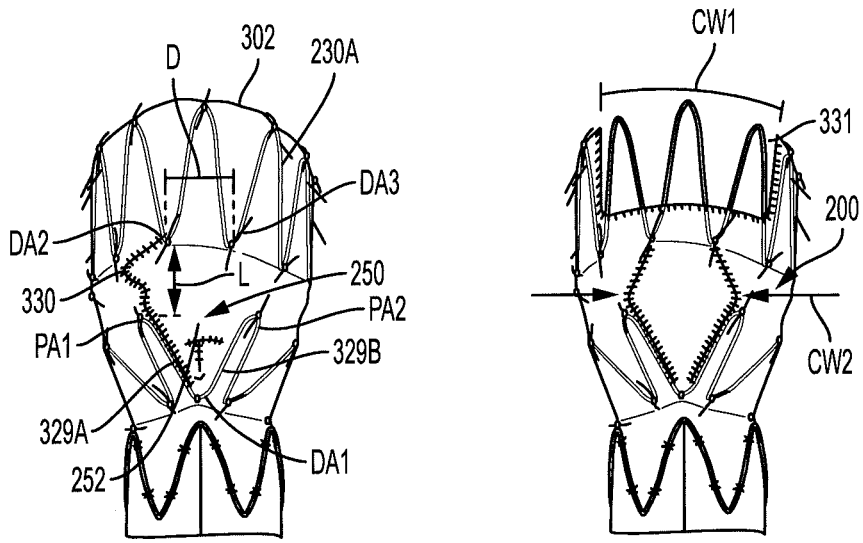
FIG. 17A depicts the prosthesis in FIG. 9 with a scalloped fenestration formed therein.

With the side branch 260 sitting freely with the main lumen 226, the side branch and trough are ready for shaping. In FIG. 17, the adjacent interconnected stent members 329A, 329B also form respective proximal apices PA1, PA2 with other interconnected stent members. Blanket stitching, shown generally as 330, may be added to capture the graft material of the trough wall 252. The trough wall 252 may be gathered or pulled to the sides and stitched to increase the tautness of the trough wall 252 in avoidance of creases or folds remaining in the trough wall. In one example, the blanket stitching 300 may start running from the distal apex DA1, up along the interconnected stent member 329A, beyond the proximal apex PA1, and through the distance L between the first and second proximal stents 230A, 230B and up to the distal apex DA2 of the first proximal stent 230A. The blanket stitching is shown to having a bent configuration between the proximal apex PA1 and the distal apex DA2. As shown in FIGS. 9-10, blanket stitching 330 may be added to capture the graft material for increased tautness at the opposite side. In one example, the blanket stitching may start running from the distal apex DA1, up along the interconnected stent member 329B, beyond the proximal apex PA2, and through the distance L between the first and second proximal stents 230A, 230B and up to the distal apex DA3 of the first proximal stent 230A. The adjacent distal apices DA2, DA3 may be spaced from another by a circumferential or lateral distance D. The circumferential center of the distance D may be in alignment with the center of the distal apex DA1. The blanket stitching is shown to having a bent configuration between the proximal apex PA2 and the distal apex DA3.

With additional reference to FIG. 10, the trough boundary 255 is shown having an unobstructed region U at the distance D between the distal apices DA2, DA3. For example, at least a portion of the proximal axial side 255A may be unobstructed from stitching and/or trough frames. For example, the region U may remain stitchless and frameless. To this end, the stitching forming the trough boundary 255 may be discontinuous and/or the trough frame, if employed, may partially enclose the trough 250. This configuration may leave the branch lumen facing surface of the trough wall 252 and one of the proximal or distal sides of the trough boundary 255 free and unobstructed, thereby providing an unobstructed surface and transition between the trough 250 and the sidewall 225. In the example shown, the branch lumen facing surface of the trough wall 252 is a continuous surface with the outer surface of the sidewall 225 of the graft body 220. Accordingly, as a device passes through the side branch 260, the tip of the device slidably contacts the branch lumen facing surface 252A of the trough wall 252. The path along this surface allows the device the capability of sliding radially and longitudinally outward (or inward) along the surface path beyond the proximal side 255A of the trough 250 to outside (or inside) the prosthesis without snagging or otherwise impeding the advancement of such device.

Figure 9A:
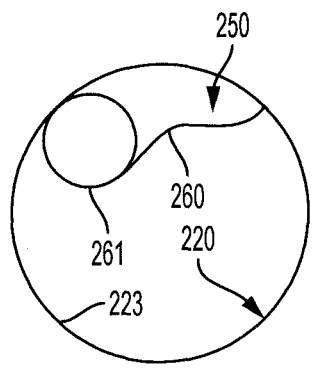
FIG. 9A is a cross-sectional view taken along lines 9A-9A in FIG. 9, depicting the helical nature of the side branch.
Figure 9B:
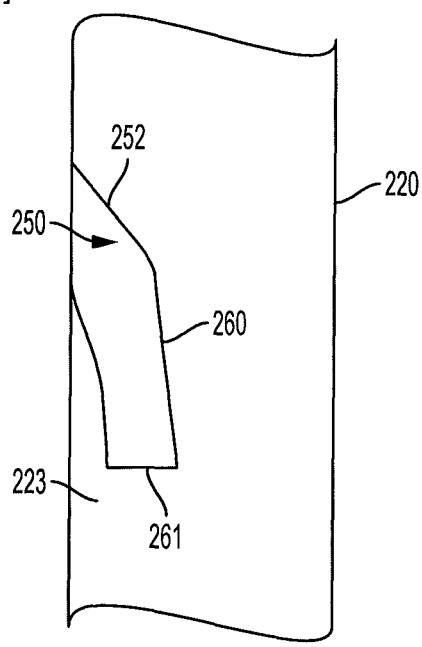
FIG. 9B is a cross-sectional view taken along lines 9B-9B in FIG. 9, depicting the helical nature of the side branch.

FIGS. 9-10 illustrate the prosthesis 200 in a final form with the side branch 260 and the trough wall 252 extending from the graft body 220. The side branch 260 is positioned in a retrograde configuration such that the second edge 316A that defines the distal end 261 of the side branch 260 is positioned closer to the outflow end 228 than the position of the trough 250. The side branch 260 may be placed in a helical configuration along the inner surface 223 of the sidewall 225, being disposed longitudinally and circumferentially. Suture stitches 265 may be utilized to fix the helical configuration. FIGS. 9A-9B depict the internal of the side branch 260 in the helical configuration and the relative position of the distal end 261 along the walls of the side branch. The side branch is shown extending helically from the trough within the main lumen in a direction away from the inflow end of the graft main body.

Figure 18:
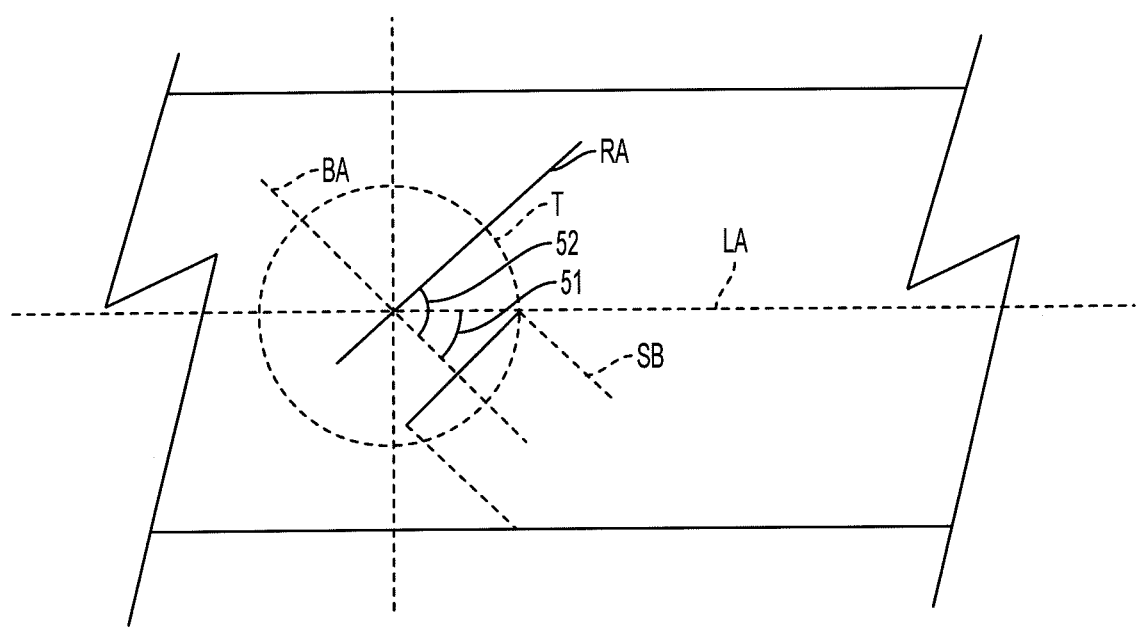
FIG. 18 depicts the approach angle of the side branch relative to the trough.

FIG. 18 illustrates an approach angle of the side branch SB for any of the disclosed protheses. When the side branch SB is in a helical configuration the approach angle is softened by skewing the branch axis BA at the outlet end of the side branch SB into the trough T from (i) the side instead of longitudinally aligned with the longitudinal axis LA and/or (ii) a more radial position instead of an axial position along the sidewall. In other words, the approach angle, defined by angle S1 and/or angle S2, may be skewed obliquely up to ninety degrees from the longitudinal axis by an angle S1 and/or by an angle S2 less than ninety degrees between the branch axis BA and a radial axis RA extending orthogonal from the longitudinal axis LA through the trough center. This approach angle configuration may allow for easier cannulation of the branch vessel and may reduce the angulation of the connected prosthesis between the side branch and the branch vessel.

Any one of the disclosed prostheses, such as, for example, prosthesis 10 or 200, may include a scalloped fenestration define along the inflow end of the graft body. The scalloped fenestration, such as, for example, the scalloped fenestration 80 in FIG. 1 and the scalloped fenestration 280 (shown in dashed lines) in FIG. 9, may be configured to accommodate the ostium or opening into another branch vessel, such as the left common carotid artery, when the trough of the prosthesis is aligned with the ostium of the branch vessel, such as the left subclavian artery. In one example, the scalloped fenestration 80 or 280 may be a notch formed in the inflow end by a cutting operation in the graft material. The scalloped fenestration 80 or 280 may have a rectangular or trapezoidal cross-sectional shape. The scalloped fenestration formed may be circumferentially centered in alignment with the center of the trough. The circumferential width of the scalloped fenestration of any one of the disclosed prostheses may wider than the circumferential width of the trough. For example, as shown in FIG. 1, the circumferential width CW1 of the scalloped fenestration 80 defined by the inflow end 27 is wider than the circumferential width CW2 of the trough 50. In one example, the circumferential width CW1 may be selected from a range of 140 to 160 degrees, and the circumferential width CW2 may be selected from a range of 50 to 70 degrees. In one example, the circumferential width CW1 is up to three times, and in some instances, two to three times larger than the circumferential width CW2. To this end, the relatively wider scalloped fenestration may accommodate various branch vessels having non-aligned angle of incidences with the main vessel. For example, in some instances, the circumferential widths selected may accommodate at least 90% of patients, where the left subclavian artery and the left common carotid artery may intersect the aortic arch at different angles, where looking along the aortic arch axis these arteries may form a V-shape. The distal end of the scalloped fenestration may be spaced from the proximal end of the trough by about 10 mm, in some examples. FIG. 17A depicts the prosthesis 200 having a scalloped fenestration 331 with the first circumferential width CW1 of about 150 degrees, and the trough with the circumferential width CW2 of about 60 degrees.

Figure 19:
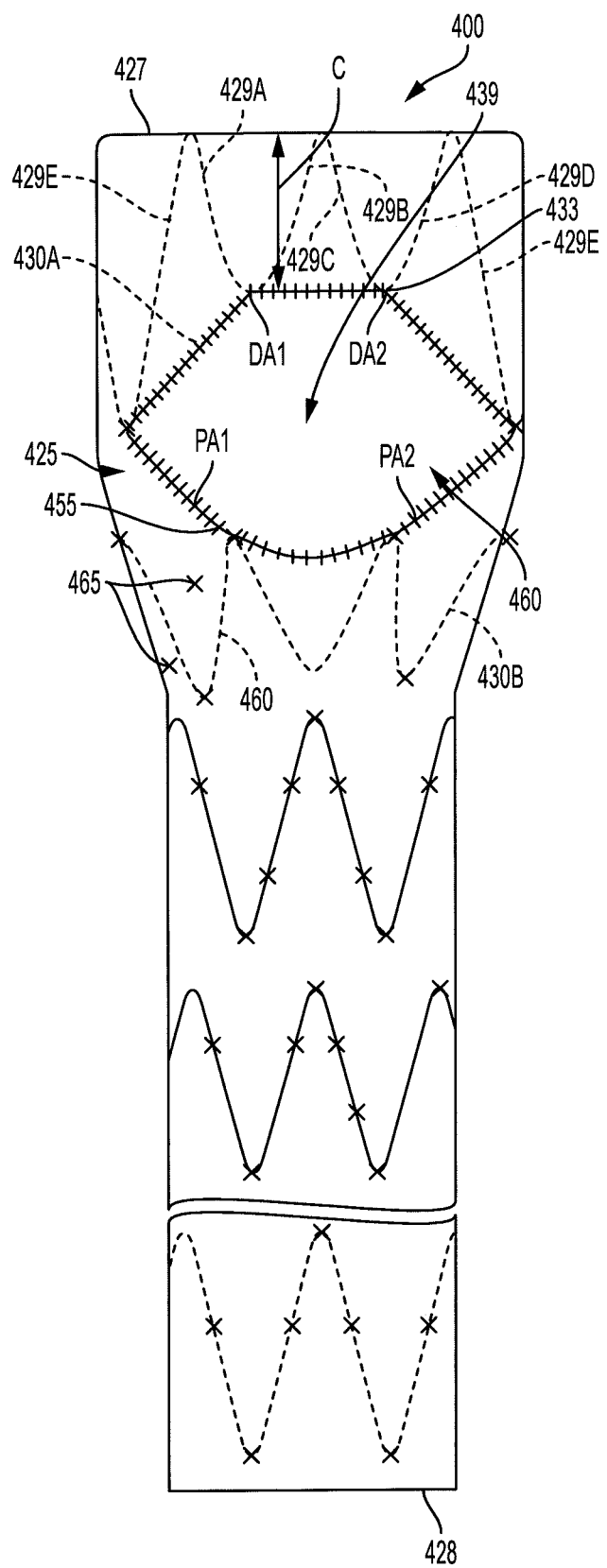
FIG. 19 is a side view of another example of a prosthesis having one example of a trough in communication with a side branch.

FIG. 19 illustrates another prosthesis 400 having similar features as the prostheses 10, 200 disclosed herein and thus similar terms will be used in the description of the prosthesis 400. The internal first proximal stent 430A includes a recessed segment 439 into which the trough 450 extends. The recessed segment 439 may be located along a distal end 433 of the first proximal stent 430A. A few (two or more) adjacent stent members 429A, 429B, 429C, 429D may be shorter in length than the remaining stent members 429E to axially offset in the proximal direction one or more distal apices DA1, DA2 relative to the other distal apices. The relative length of the shorter stent members may be up to about 70% of the length of the remaining stent members. In one example, the shorter stent members may be about 10 to 15 mm and the length of the remaining ones is 20 mm. The recessed segment 439 is sized to receive at least a proximal portion of the trough 450 such that the trough 450 may be placed at a distance C closer to the inflow end 427, for example, about 10-15 mm, from the inflow end 427 of the prosthesis 400. In some examples, the relative closer position of the trough 450 may eliminate a scalloped fenestration. The axial length of the recessed segment may still allow for suitable sealing between the proximal end of the prosthesis and the corresponding vessel wall.

The trough 450 and the side branch 460 may be formed similar to the formation of the trough and the side branch in any of the figures, such as, for example, in FIGS. 3-8. The size and shape of the trough may vary depending on the application. In one example, the cutout that defines the trough boundary 455 may extend between the distal apices DA1, DA2, extend tapering outward to adjacent distal apices of the remaining stent members 429E, extend tapering inward to and along the proximal apices PA1, PA2 of the second proximal stent 430B, and extend between the proximal apices PA1, PA2. In another example, the trough 450 may be sized smaller than the spacing defined by the recessed segment 439. After attachment of the trough 450 and the side branch 460, the side branch 460 may be positioned in a desired location. For example, the side branch 460 may be positioned in a retrograde configuration such that the end of the side branch 460 that is opposite the trough 450 is positioned closer to the outflow end 428 than the position of the trough 450. The side branch 460 may be placed in a helical configuration along the inner surface of the sidewall 425, being disposed longitudinally and circumferentially. Suture stitches 465 may be utilized to fix the helical configuration.

Barb or anchoring structures may be provided on any one of the disclosed prostheses, such as for example, prosthesis 10, 200 or 400, to anchor the prosthesis to the body vessel and inhibit migration of the prosthesis. For example, returning to FIG. 1, the outer annular proximal bare region 42 and/or the annular distal bare region 51 along the outer surface 24 of the graft body 20 may not include a support stent structure, but may include barb or anchoring structures 47. Such barbs 47 may also prevent possible crushing of any internal or external portions of the graft (such as the branch) that may result from the graft collapsing or kinking within the vessel. Barbs 247 are also shown disposed through the graft body 220 in FIG. 9.

One or more radiopaque markers may be included to provide radiographic visualization of the position of any one of the prostheses disclosed herein when placed in a body vessel of a patient. A plurality of radiopaque markers, which according to one example may be provided in the form of gold beads, may be coupled to any portion graft body for desired visualization. In one example, as shown in FIG. 1, illustrates a plurality of the radiopaque markers R disposed along the boundary of scalloped fenestration.

It is further contemplated that any one of the prostheses disclosed herein may have multiple side branches within any one of the trough configurations. For example, the prosthesis may have two, three, or more branches attached to the graft body. The various branches may be positioned at different longitudinal and circumferential positions along the graft body. In this manner, the side branches may be configured to align with, for example, the left subclavian, left common carotid, and/or inanimate arteries. Additionally, or alternatively, the prosthesis may be configured for placement at various other positions within the vasculature of the patient.

Rather than attaching the side branch in a particular orientation, additionally, or alternatively, the trough of any one of the disclosed prostheses may enable movement of the side branch relative to the graft body. For example, the trough may be configured to enable the material of the trough walls to move (for example, inward or outward with respect to the longitudinal axis of the graft body). The opening of the second end of the side branch may be directed in any direction (for example, proximal, distal, or transverse) relative to the longitudinal axis of the graft body. For example, the side branch may be configured to pivot about the trough between the retrograde configuration and the antegrade configuration.

The main graft body of any one of the disclosed prostheses may have a diameter, for example, ranging from about 10 mm to about 50 mm, typically from about 22 mm to about 46 mm, and a length of about 10 cm to about 200 cm. As described, the diameter of the graft body may be constant along the length thereof. Alternatively, the graft body may be tapered, such as shown, and may taper down 10 mm along a length. A tapered graft body may be advantageous for placement within a narrowed aorta. Such a narrowed aorta may be common when treating aortic dissection. The side branch may have a diameter, for example, ranging from about 6 mm to about 24 mm, typically from about 8 mm to about 12 mm, and having a length about 8 mm to about 25 mm. The diameter of the side branch may be constant along the length thereof. Alternatively, the side branch may be tapered such that the diameter of the side branch may vary along the length thereof. In other examples, the side branch may have any suitable diameter and/or length.

Any one of the disclosed prostheses may be configured for placement in the aortic arch and/or in the descending thoracic aorta. The trough may be aligned with a branch vessel, such as the brachiocephalic, left subclavian and/or left common carotid arteries. There may be additional fenestrations formed in the main graft body, as desired, to align with additional branch vessels, to restore patency or otherwise provide flow thereto. Once placed in the aorta, flow into a branch vessel, such as the left common carotid artery and/or left subclavian artery, may not be impeded and may continue through both the trough and the scalloped fenestration. It is also contemplated that the prosthesis may be placed in other portions of the aorta such that the trough aligns with other branch vessels in the aortic arch to allow deployment of an external side branch connector stent graft therein, if needed, while the scalloped fenestration may accommodate and allow flow to continue into other branch vessels when the prosthesis is in place.

Figure 20:
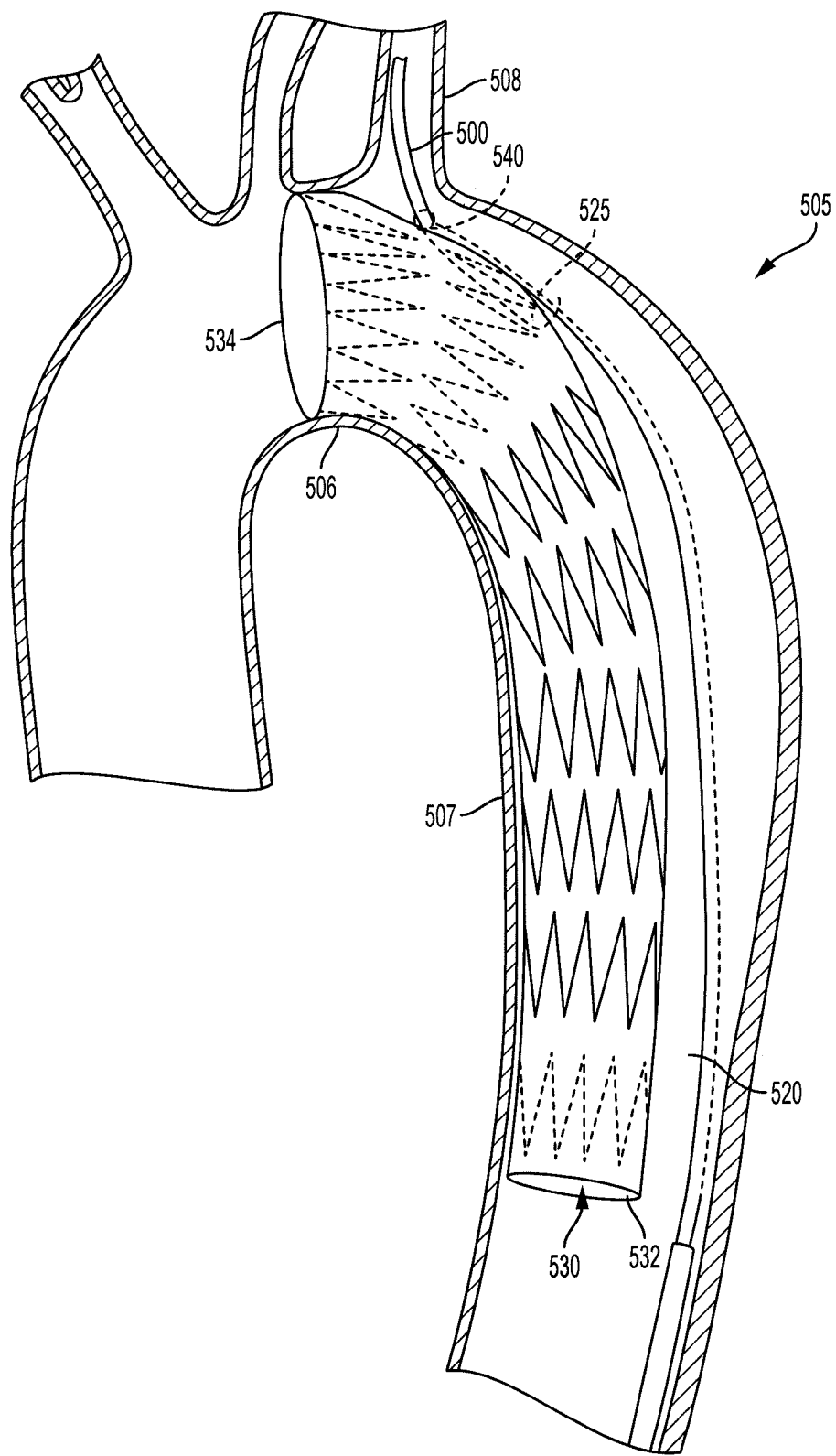
FIG. 20 depicts a catheter passing through a trough and a side branch of a prosthesis into a branch vessel, where the prosthesis is implanted into a primary body vessel.
Figure 21:
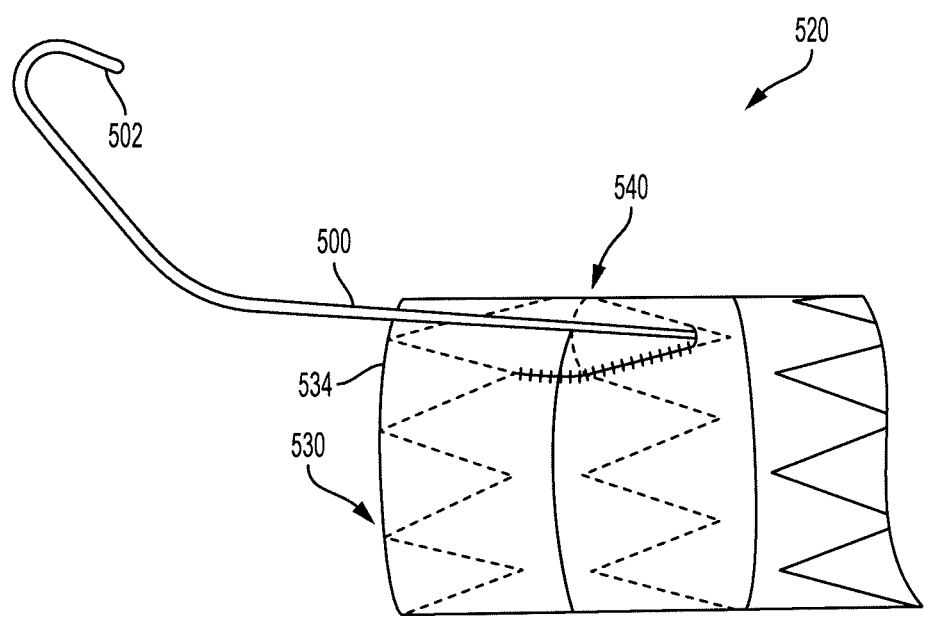
FIG. 21 depicts a catheter passing through a trough and a side branch of a prosthesis.
Figure 22:
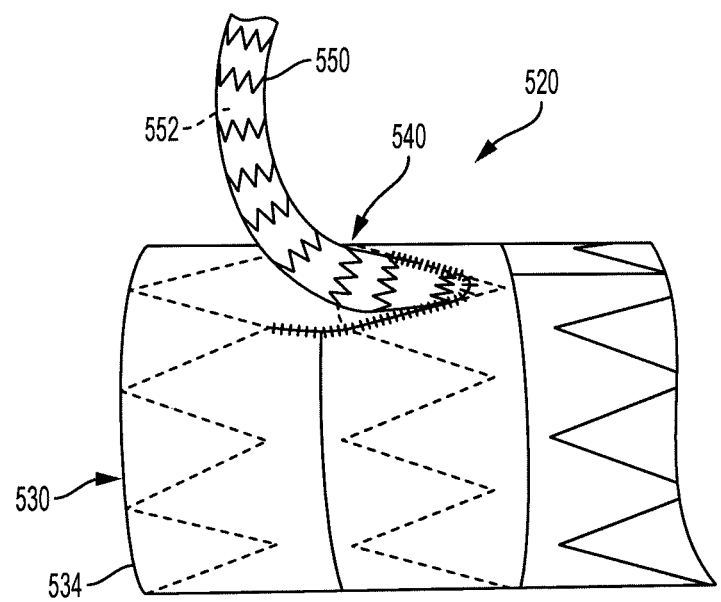
FIG. 22 depicts a connection prosthesis extending out from a trough and a side branch of a prosthesis and implanted within a branch vessel.

As shown in FIGS. 20-22, catheters or other devices may be inserted though the side branch and out the trough of any one of the disclosed prostheses 10, 200, or 400 (now referred to as prosthesis 520) to access a part of the anatomy. The anatomy may include various configurations including a main vessel and one or more branch vessels. The anatomy 505 shown is the aorta including the aortic arch 506 and the descending aorta 507. The left subclavian 508 is shown branching from the aorta. Such devices may be inserted through the vessels after the expansion of the prosthesis 520 or may be preloaded as described. As shown, a catheter 500, which may be configured to facilitate cannulation of a branch vessel, movement of the side branch 525 of the prosthesis 520, and/or insertion of a branch prosthesis within the side branch. The catheter 500 may be preloaded in the prosthesis 520 prior to introduction of the prosthesis within a patient. When preloaded as part of a delivery system, a proximal region 502 of the catheter 500 may be advanced through the main lumen 530 of the prosthesis from the outflow end 532 toward the inflow end 534. The proximal region 502 of the catheter 500 then may be advanced through the side branch 525 to exit the prosthesis 520 from the trough 540, as shown in FIG. 21. This configuration of the preloaded catheter (i.e., extending proximally within the prosthesis from the outflow end) may be desirable for retrograde delivery of the prosthesis (for example, femoral delivery). In other examples, the catheter 500 may be advanced through the main lumen from the inflow end toward the outflow end. This configuration of the preloaded catheter (i.e., extending distally within the prosthesis from the inflow end) may be desirable for antegrade delivery of the prosthesis (for example, brachial, axillary, or transapical delivery). The catheter 500 may sit in a separate groove in a tip of a delivery device. It can be appreciated that pulling back an outer sheath may expose the catheter 500 to allow a physician to snare and withdraw the preloaded catheter through a sheath in the subclavian artery. In other examples, the catheter 500 may include a catch member such as a hook, loop, or eye at the proximal region 502 to aid the physician in snaring the catheter 500. Additionally, or alternatively, a guidewire (now shown) may be received within a lumen of the catheter 500. The guidewire may be preloaded in the prosthesis 520 with respect to the catheter 500 and/or received within the catheter. The guidewire may facilitate the placement of various other devices, devices, or components (for example, the balloon described below) within the vasculature of the patient.

The prosthesis 520 may be radially compressed into a delivery configuration and mounted onto a deployment device and maintained in the delivery configuration by a retractable outer sheath, as known. Any type of deployment device suitable for deploying the loaded prosthesis may be used. Although the following description will generally refer to femoral delivery of the prosthesis 520, the prosthesis also may be delivered via subclavian delivery, brachial delivery, transapical delivery, axillary delivery, or any other desirable form of delivery. A person having ordinary skill in the art will appreciate that the configuration and/or orientation of the prosthesis, the delivery device, the catheter, and/or any components thereof may be modified depending on the chosen delivery method. Such modifications are within the scope of this disclosure. To deploy the prosthesis 520, the operator may slide or retract the outer sheath over the deployment device, thereby exposing the prosthesis. The prosthesis 520 may radially expand outwardly upon removal of the sheath. The operator may directly manipulate the outer sheath, which may provide the operator with a relatively high degree of control during the procedure. Further, such deployment devices may be compact and may have a relatively uniform, low-diameter radial profile, allowing for atraumatic access and delivery.

Using such a suitable deployment device, a physician may introduce the prosthesis 520 in the delivery configuration into the femoral artery and guide the prosthesis 520 into position within the aortic arch 506 and/or the descending aorta 507. The prosthesis. 520 may be positioned using the radiopaque markers such that the side branch 525 is generally aligned in the vicinity of the ostium of the left subclavian artery 508. The prosthesis 520 may remain at least partially restrained in a radially compressed configuration, for example, by one or more diameter reducing ties. The diameter reducing ties may be applied to the proximal and distal stents to retain the inflow and outflow ends in a reduced diameter configuration after retraction of the sheath, such as by tied thread and trigger wire arrangement. The stent members may be released upon removal of the trigger wire to allow expansion of the stent. The diameter reducing ties also may be configured as any other type of constraining member capable of reducing the diameter of a stent of the prosthesis.

Retraction of the outer sheath also may expose the catheter 500, when preloaded, extending from the side branch 525 and the trough 540 of the prosthesis 520, as shown in FIG. 21. Otherwise, the catheter 500 may be advance to the position after prosthesis expansion. The catheter 500 may be snared and pulled though a sheath positioned within the left subclavian artery 508. A balloon may be tracked over the catheter 500 and positioned within the side branch 525. The balloon may be manipulated to adjust the orientation of the side branch 525 relative to the graft body of the prosthesis 520. In one example, a first end of the balloon may be positioned and movable within the main lumen of the graft body of the prosthesis 520 to move the side branch, if desired.

The trough and side branch configuration of any one of the disclosed prostheses may be beneficial for providing a tracking path for passing devices such as the catheter 500 from the side branch, along the trough wall and outside the prosthesis. The relative size, shape, and/or position along the tapered section, as well as, in some instances, a relatively continuously smooth surface (that is, without stitching) along the trough wall and/or the omission of stitching, frame or other obstruction from the trough boundary may provide a smooth transition surface between the trough and the sidewall. The operator physician may pass devices, such as wires, catheters and sheaths, through the side branches easier and more efficiently to speed of the operation time when using helical retrograde configured side branches. The positioning of the trough along a tapered segment of the main graft body may create a larger void between the body vessel wall and the graft wall in which to maneuver and position pass-through devices and connecting stent grafts. This trough positon in combination with the side branches in a helical configuration and retrograde configuration, such as shown, may provide easier cannulation and less binding potential when proximally advancing a device through the internal helical side branch and out of the trough for insertion into a side branch.

It can be appreciated that a branch prosthesis 550, such as a stent graft, may be deployed within the side branch 525 and out the trough 540 of the prosthesis 520, as shown in FIG. 22. The branch prosthesis 550 may be delivered over the catheter 500 and deployed within the side branch using any known method. The branch prosthesis 550 may extend longitudinally, for example, proximally from the side branch, relative to the graft body. The branch prosthesis 550 may extend between a position within the main lumen of the graft body and a position external to the graft body. A lumen 552 of the branch prosthesis 550 may be in communication with the main lumen of the prosthesis 520. In one example, the branch prosthesis 510 may extend between the main lumen of the prosthesis 520 and a branch vessel such as the left subclavian artery 508. In other words, a first end of the branch prosthesis 550 may be deployed within the branch lumen of the side branch 525 and a second end of the branch prosthesis 550 may be deployed within the left subclavian artery 508. In this manner, the branch prosthesis 550 may couple the prosthesis 520 to the left subclavian artery 508 to create a continuous fluid passageway therebetween. The branch prosthesis 550 may be configured for other vessels, including but not limited to a brachiocephalic, and/or left common carotid artery.

The term "graft" describes an object, device, or structure that is joined or that is capable of being joined to a body part to enhance, repair, or replace a portion or a function of that body part. Grafts that can be used to repair body vessels include, for example, films, coatings, or sheets of material that are formed or adapted to conform to the body vessel that is being enhanced, repaired, or replaced. The graft material may be formed from a biocompatible material that is substantially non-toxic in the in vivo environment of its intended use and substantially unrejected by the patient's physiological system (i.e., is non-antigenic). In non-limiting examples, the graft material may be made of any one or combination of: an expanded polytetrafluoroethylene (ePTFE), polytetrafluoroethylene (PTFE), silicone, polyurethane, polyamide (nylon), fabric graft materials, for example, woven polyester, polyetherurethanes, polyethylene, a bioremodelable material such as reconstituted or naturally-derived collagenous materials, extracellular matrix (ECM) material, submucosa.

The delivery systems described herein may need various other components in order to obtain a delivery and deployment system that is optimally suited for its intended purpose. These include and are not limited to various outer sheaths, pushers, trigger wires, stoppers, guide wires, and the like. For example, the Zenith® Thoracic Aortic Aneurysm Endovascular Graft uses a delivery system that is commercially available from Cook Inc., Bloomington, Ind., and may be suitable for delivering and deploying an aortic prosthesis in accordance with the present embodiments.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:

1. A prosthesis, comprising:
a tubular graft main body including a sidewall extending between an inflow end and an outflow end, and a main lumen extending between the outflow end and inflow end about a graft longitudinal axis, the graft main body including an inflow end segment, an outflow end segment, and an intermediate tapered segment interconnecting the inflow end segment and the outflow end segment, wherein the inflow end segment has a larger cross-sectional area than the outflow end segment;
a trough comprising a trough boundary having a proximal axial side and a distal axial side distal of the proximal axial side and forming an apex, and a trough wall, the trough wall extending radially inwardly and substantially longitudinally from the sidewall at the proximal axial side along the intermediate tapered segment and at least partially within an inner lumen of the tubular graft main body; and
a tubular graft branch having a substantially circular proximal opening, a distal opening, and branch lumen extending therein, the tubular graft branch extending from the distal axial side of the trough wall and within the main lumen in a helical pattern in a direction away from the inflow end of the graft main body and configured to receive retrograde flow, wherein the trough, the branch lumen, and the main lumen are in fluid communication, wherein the trough wall has a length extending between an outer surface of the side wall proximal of the tubular graft branch and the tubular graft branch, and wherein the proximal opening is disposed immediately adjacent the apex, wherein at least a portion of the proximal axial side is unobstructed, thereby providing a continuous unobstructed surface and transition between the trough wall and the sidewall from an outer surface of the side wall to a branch lumen facing surface of the trough wall.

2. The prosthesis of claim 1, further comprising a plurality of stents coupled along the graft main body, each of the stents including a plurality of interconnected stent members, wherein at least a portion of the trough is disposed between a pair of adjacent stent members of one of the stents.

3. The prosthesis of claim 2, wherein the trough is defined by a trough boundary formed at the sidewall of the graft main body, wherein at least a portion of the trough boundary includes stitching along at least one of the pair of adjacent stent members.

4. The prosthesis of claim 3, wherein the trough boundary includes a stitchless and frameless portion along the proximal axial side of the trough.

5. The prosthesis of claim 1, further comprising a proximal stent coupled along the inflow end segment of the graft main body, the proximal stent including a plurality of stent members interconnected at proximal and distal apices, wherein the trough is defined by a trough boundary formed at the sidewall of the graft main body, and a portion of the trough boundary is disposed along a pair of adjacent distal apices of the proximal stent.

6. The prosthesis of claim 5, wherein a length of the stent members defining the pair of adjacent distal apices is shorter than a length of remaining stent members of the proximal stent.

7. The prosthesis of claim 1, wherein the graft branch and the trough are integrally comprised of a common graft material that is coupled to the graft main body.

8. The prosthesis of claim 7, wherein the trough is stitched along a multi-sided opening formed in the sidewall of the graft main body.

9. The prosthesis of claim 1, wherein the graft branch, the trough, and the graft main body are integrally comprised of a common graft material, wherein the trough and the graft branch are in an inverted relationship relative to the graft main body.

10. The prosthesis of claim 1, wherein a scalloped fenestration is formed along the inflow end.

11. The prosthesis of claim 10, wherein the scalloped fenestration is sized to extend beyond the trough in both circumferential directions.

12. The prosthesis of claim 1, wherein the graft branch includes a branch axis, wherein the branch axis at an end of the graft branch associated with the trough is skewed relative to the graft longitudinal axis.

13. The prosthesis of claim 12, wherein a radial axis extends orthogonal from the graft longitudinal axis through a center of the trough, wherein the branch axis at said end of the graft branch associated with the trough extends obliquely relative to the radial axis.

14. A prosthesis, comprising:

a tubular graft main body including a sidewall extending between an inflow end and an outflow end, and a main lumen extending between the outflow end and inflow end about a graft longitudinal axis, the graft main body including an inflow end segment, an outflow end segment, and an intermediate segment interconnecting the inflow end segment and the outflow end segment;

an opening in the sidewall in the intermediate segment;

a trough of graft material defining a trough wall having a proximal axial side and a distal axial side distal of the proximal axial side forming a distal axial side apex, and a trough wall; and a tubular graft branch having a substantially circular proximal end opening, a distal end opening, and a branch lumen extending therein, the tubular graft branch extending from the distal axial side of the trough wall and within the main lumen in a helical pattern in a direction away from the inflow end of the graft main body and configured to receive retrograde flow, wherein the trough, the branch lumen, and the main lumen are in fluid communication, and wherein the proximal end opening is disposed immediately adjacent the distal axial side apex;

wherein the tubular graft branch, the trough, and the graft main body are integrally comprised of a common graft material formed from a single piece of graft material, wherein the trough and the graft branch are in an inverted relationship relative to the graft main body;

and wherein at least a portion of the proximal axial side is unobstructed, thereby providing a continuous unobstructed surface and transition between the trough wall and the sidewall from an outer surface of the sidewall to a branch lumen facing surface of the trough wall.

15. A prosthesis, comprising:

a tubular graft main body including a sidewall extending between an inflow end and an outflow end, and a main lumen extending between the outflow end and inflow end about a graft longitudinal axis, the graft main body including an inflow end segment, an outflow end segment, and an intermediate segment interconnecting the inflow end segment and the outflow end segment;

an opening in the sidewall in the intermediate segment;

a trough of graft material defining a trough boundary having a proximal axial side and a distal axial side having a distal axial side apex, and a trough wall within the boundary, the trough wall extending from the sidewall at the proximal axial side and radially inwardly from the sidewall; and a tubular graft branch having a substantially circular proximal end opening, a distal end opening, and branch lumen extending therein, the proximal end of the tubular graft branch extending from the distal axial edge of the trough wall and within the main lumen in a helical pattern in a direction away from the inflow end of the graft main body and configured to receive retrograde flow, wherein the trough, the branch lumen, and the main lumen are in fluid communication, and wherein proximal opening is disposed immediately adjacent the distal axial side apex;

wherein at least a portion of the proximal axial side is stitchless and frameless thereby providing a continuous unobstructed surface and transition between an outer surface of the sidewall and a branch lumen facing surface of the trough wall.

16. A prosthesis, comprising:

a tubular graft main body including a sidewall extending between an inflow end and an outflow end, and a main lumen extending between the outflow end and inflow end about a graft longitudinal axis, the graft main body including an inflow end segment, an outflow end segment, and an intermediate segment interconnecting the inflow end segment and the outflow end segment;

an opening in the sidewall in the intermediate segment;

a trough of graft material defining a trough boundary having a proximal axial side and a distal axial side defining an apex, and a trough wall extending radially inwardly from the sidewall at the proximal axial side; and a tubular graft branch having a substantially circular proximal open end, a distal open end, and a branch lumen extending therein, the tubular graft branch extending from distal axial side of the trough wall and within the main lumen in a helical pattern in a direction away from the inflow end of the graft main body and configured to receive retrograde flow, wherein the trough, the branch lumen, and the main lumen are in fluid communication;

wherein the tubular graft branch, the trough, and the graft main body are integrally comprised of a common graft material formed from a single piece of graft material;

wherein the proximal open end is disposed immediately adjacent the apex, and wherein at least a portion of the proximal axial side is stitchless and frameless thereby providing a continuous unobstructed surface and transition between an outer surface of the sidewall and a branch lumen facing surface of the trough wall.

* * * * *